(12) United States Patent
Fiala

(10) Patent No.: US 6,536,899 B1
(45) Date of Patent: Mar. 25, 2003

(54) MULTIFOCAL LENS EXHIBITING DIFFRACTIVE AND REFRACTIVE POWERS

(75) Inventor: Werner Fiala, Vienna (AT)

(73) Assignee: Bifocon Optics GmbH, Vienna (AT)

( * ) Notice: Subject to any disclaimer, the term of this patent is extended or adjusted under 35 U.S.C. 154(b) by 177 days.

(21) Appl. No.: 09/613,470

(22) Filed: Jul. 11, 2000

Related U.S. Application Data

(63) Continuation of application No. 09/489,353, filed on Jan. 21, 2000, now abandoned.
(60) Provisional application No. 60/143,718, filed on Jul. 14, 1999.

(51) Int. Cl.[7] .............................. G02C 7/06; G02C 7/04; G02B 27/44; G02B 5/08; A61F 2/16
(52) U.S. Cl. ..................... 351/168; 351/161; 359/565; 359/838; 623/6.3
(58) Field of Search .......................... 359/565, 838; 351/168, 161, 177; 623/6.3

(56) References Cited

U.S. PATENT DOCUMENTS

| | | |
|---|---|---|
| 4,210,391 A | 7/1980 | Cohen |
| 4,338,005 A | 7/1982 | Cohen |
| 4,655,565 A | 4/1987 | Freeman |
| 4,830,481 A | 5/1989 | Futhey et al. |
| 4,881,804 A | 11/1989 | Cohen |
| 4,898,461 A | 2/1990 | Portney |
| 4,995,714 A | 2/1991 | Cohen |
| 4,995,715 A | 2/1991 | Cohen |
| 5,760,871 A | 6/1998 | Kosoburd et al. |

FOREIGN PATENT DOCUMENTS

| | | |
|---|---|---|
| EP | 0 354 786 A2 | 2/1990 |
| EP | 0 470 811 A2 | 2/1992 |
| EP | 0 605 841 A1 | 7/1994 |
| WO | WO 95/25288 | 9/1995 |

Primary Examiner—Scott J. Sugarman

(57) ABSTRACT

A multifocal lens including annular zones wherein each annular zone is divided into at least two annular sub-zones. Preferably, no geometric or optical optical steps are present between annular zones or annular sub-zones. The refractive powers within the annular sub-zones are chosen such that the lens exhibits at least two diffractive powers and that at least one of those diffractive powers substantially coincides with the average refractive power of each annular zone.

32 Claims, 12 Drawing Sheets

IDEAL          PRACTICAL

IDEAL          PRACTICAL

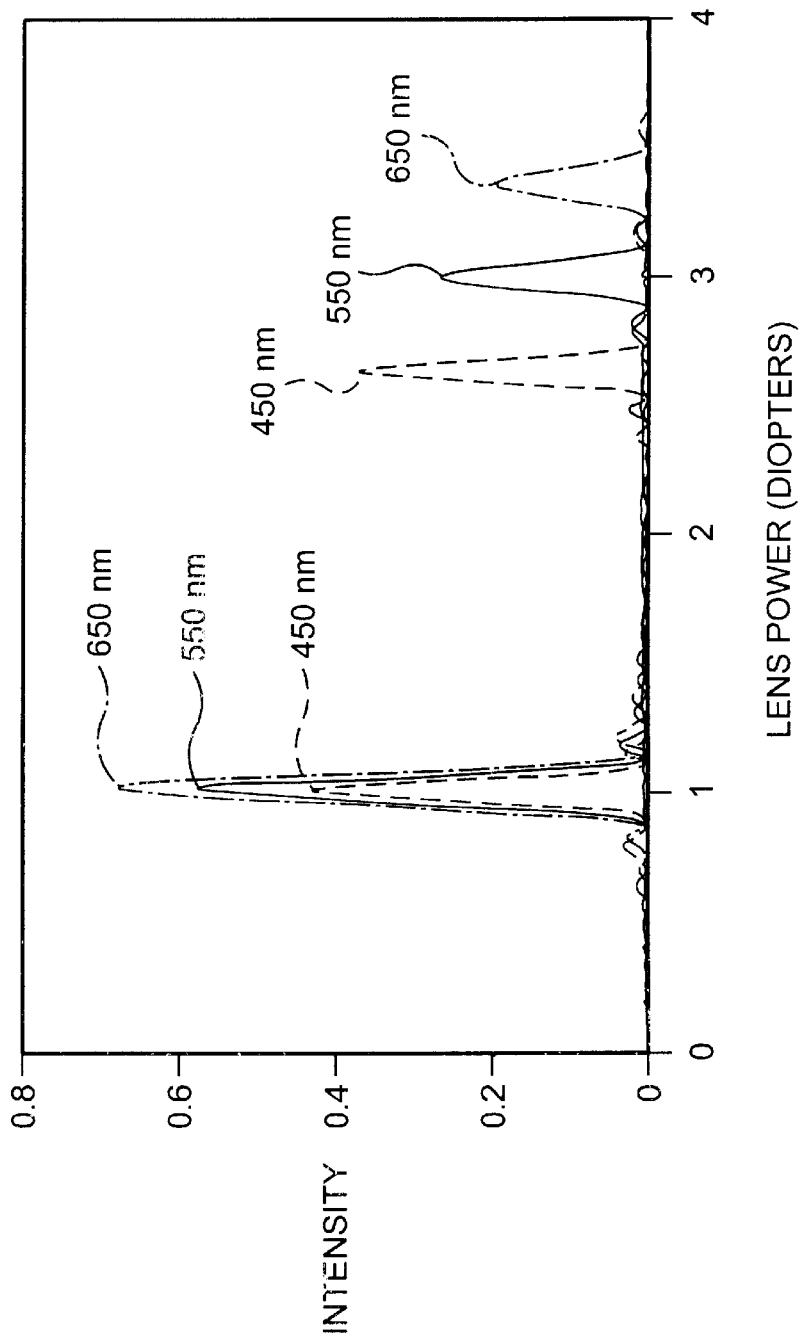
FIG. 8  TFR OF A MULTIFOCAL LENS WITH 16 ZONES ON 5.93mm DIAMETER AND SMOOTH OUTER SURFACES. EACH ZONE EXHIBITS POWER 2 (IN 80%) AND -3D (IN 20%) OF ZONE AREA.

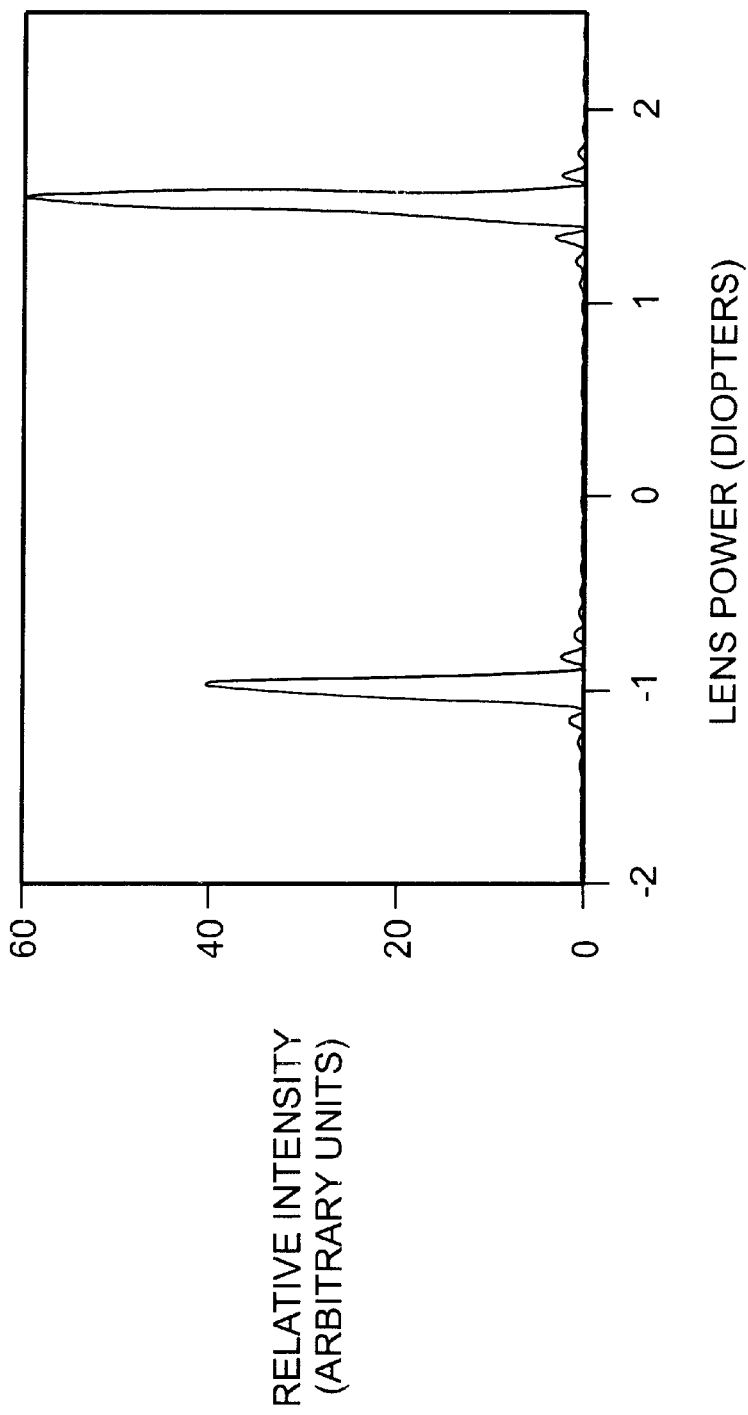
FIG. 9  MULTIFOCAL LENS WITH TWO MAIN POWERS -1 AND 1.5 DIOPTERS
LENS SPECIFICATIONS : SEE TEXT

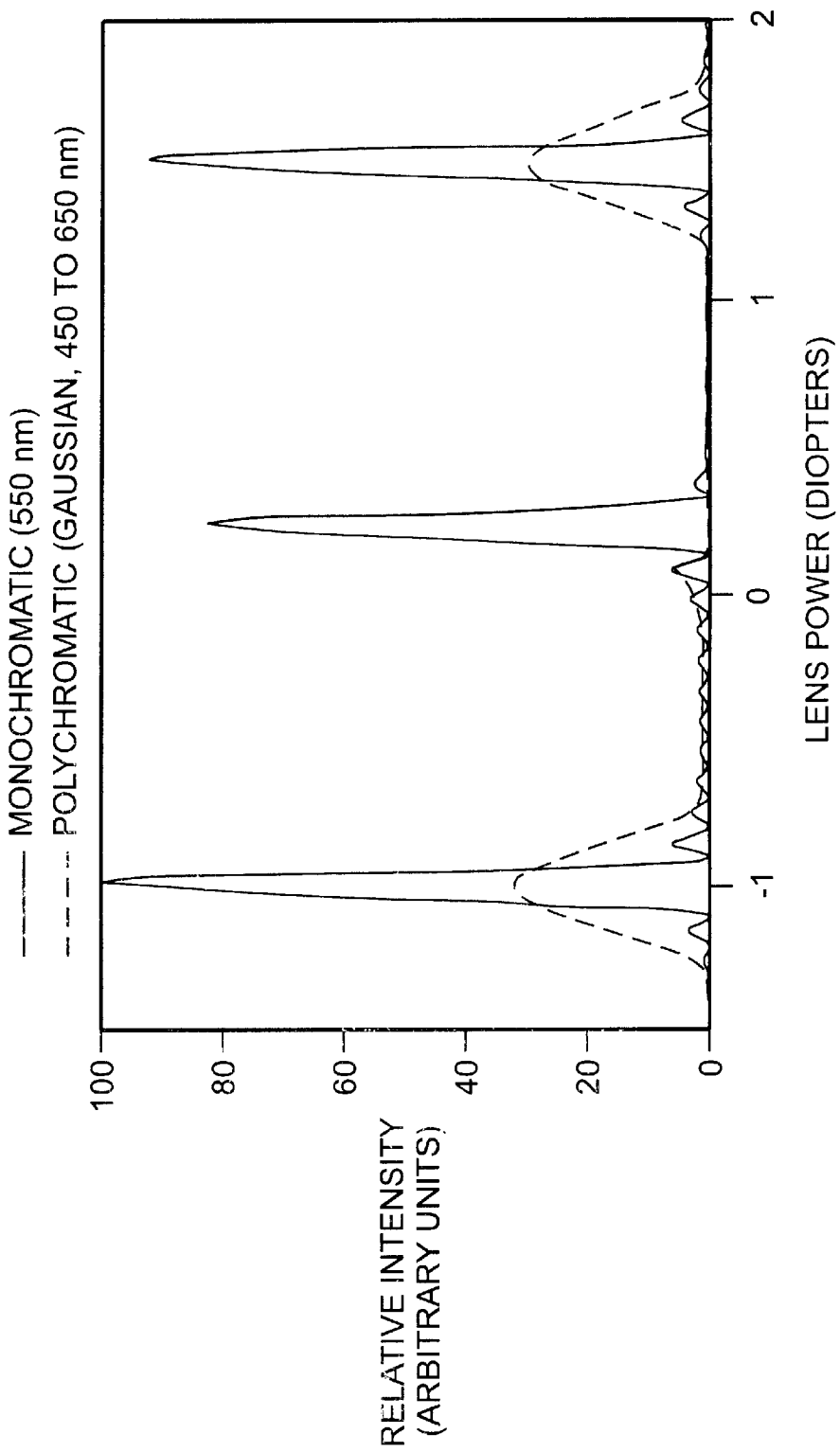
FIG. 11 TRIFOCAL LENS EXHIBITING 24 FRESNEL ZONES ON A 6.5 mm DIAMETER WITH INDEPENDENT RELATIVE INTENSITIES IN THREE POWERS FOR LIGHT OF 550 nm WAVELENGTH (SEE TEXT)

FIG. 13 TFR OF TWO LENSES WITH MAIN POWERS 0 AND 2 DIOPTERS

FIG. 14 TFR OF A NORMAL LENS AND A MODIFIED LENS - LENS DIAMETER: 6 mm
NORMAL LENS: TYPE A LENS, ALL ZONES ARE FRESNEL ZONES
MODIFIED LENS: TYPE A LENS, INNER ZONES SMALLER THAN OUTER ZONES (SEE TEXT)

FIG. 15  TFR OF A NORMAL LENS AND A MODIFIED LENS - LENS DIAMETER: 2.5 mm
NORMAL LENS: TYPE A LENS, ALL ZONES ARE FRESNEL ZONES
MODIFIED LENS: TYPE A LENS, INNER ZONES SMALLER THAN OUTER ZONES (SEE TEXT)

MULTIFOCAL LENS EXHIBITING DIFFRACTIVE AND REFRACTIVE POWERS

TYPE OF APPLICATION (37 C.F.R. 1.53(b))

This application is a(n):

Continuing application: Continuation-in-Part (CIP) of Ser. No. 09/489,353 filed on Jan. 21, 2000 now abandoned and this application claims the benefit of provisional application Ser. No. 60/143,718, filed Jul. 14, 1999.

BACKGROUND OF THE INVENTION

1. Field of the Invention

The present invention relates generally to multifocal lenses, and more particularly to multifocal lenses with powers which are intrinsically both diffractive and refractive powers. The invention relates even more particularly to multifocal lenses which provide simultaneous refractive and diffractive powers without exhibiting optical steps on a lens surface, common with diffractive lenses. The invention also relates to multifocal lenses in which at least two powers can be attributed to arbitrary relative intensities completely independent of one another.

2. Description of the Prior Art

A diffractive lens generally consists of any number of annular lens zones of equal area; such zones are usually called Fresnel zones. Between adjacent zones optical steps are provided with associated path length differences t which usually are absolutely smaller than a design wavelength $\lambda$. The area or size of the zones determines the separation between the diffractive powers of the lens; this separation increases with decreasing zone area. The optical path length difference t determines the relative peak intensities of the various diffractive powers, e.g. for $t=\lambda/2$ there are two principal diffractive powers, the 0-th and the 1-st order diffractive power, respectively, and both exhibit a peak intensity of $(2/\pi)^2=40.5\%$, where 100% is the peak intensity of a lens with identical Fresnel zones but with zero path length differences between any and all zones. The latter lens is a "normal" refractive lens. For absolute path length differences smaller than half the design wavelength, the zeroth order power is dominant, for $\lambda>abs(t)>\lambda/2$ the first diffractive order power carries the maximum relative intensity.

It is of paramount importance to note that with any single Fresnel lens zone of a diffractive lens, a refractive power is associated; this refractive power can be calculated by refracting an incoming light ray using Snell's refraction law. The Fresnel zone may exhibit a uniform refractive power, but it can also exhibit a certain blaze design in such a way that the refractive power of the zone varies across said zone; then the refractive power of this zone is an average power.

In conventional multifocal diffractive lenses with optical steps between adjacent zones, none of the various diffractive powers of the lens are equal to the refractive power of the zones. In particular, this is true also for the zeroth diffractive power of a diffractive lens, in apparent contradiction to the terminology used by some authors who call this zeroth diffractive power the "refractive" power of a diffractive lens (see e.g. Freeman, U.S. Pat. Nos. 4,537,697 and 4,642,112). But even if the average optical path lengths of light rays between an object point and its conjugated image point through any two zones are equal—as is the case in the zeroth order diffractive power—this power is not a refractive power, since it cannot be calculated or derived on the basis of the refraction law for light rays, i.e. without wave considerations.

There are two principal designs of diffractive lenses. In the first design, the optical path length difference t between the first and second zone is equal to the path length difference between the second and the third zone, etc. Embodiments of such diffractive lenses usually exhibit a saw tooth profile on one of the surfaces of a lens made from a material of some given refractive index. This saw tooth profile can be embedded in a material of different refractive index in order to obtain e.g. smooth outer surfaces of the bulk lens. FIG. 1 is a schematic sketch of the center portion of a diffractive lens according to such a design of the prior art. When applied to a contact lens, the saw tooth profile is usually present on the back surface of the lens in order to control the phase relations of such lenses. The saw tooth profile 4 is completely embedded in the tear layer 1 between the cornea 2 and the diffractive lens 3; thus definite conditions for the phase relations of the diffractive lens are guaranteed. The lens 3 has to be made, of course, from a material whose index of refraction is different from the refractive index of the tear fluid. Although in such a design comfort may be compromised by the presence of circular grooves on the backside, such a design is presently the only one which has obtained practical importance in ophthalmic optics. Putting the saw tooth profile on the front surface results in smaller acceptable machining tolerances, since $abs(n_L-1)$ is usually larger than $abs(n_L-n_T)$, wherein $n_L$ is the refractive index of the lens and $n_T$ the index of the tear fluid. Also, a tear layer on front grooves of a diffractive lens can compromise the optics of such a lens, since the tear layer thickness will most likely be non-uniform.

In the second principal design of prior art diffractive lenses, the optical path length differences between the first and second zone is +t; between the second and third zone is −t; between the third and forth zone is +t; etc. FIG. 2 is a schematic sketch of the central portion of a contact lens according to this prior art design, in comparison with FIG. 1. Although it would seem that such a lens rests more comfortably on the eye, contact lenses of this design have not gained major practical importance. The reasons for this are likely to be of practical nature, since it is difficult to cut such lenses or molds for such lenses. More specifically, two adjacent comers 5 and 6 of any zone would have to be cut by diamond tools of different orientation, since the groove cross-section should be rectangular and not trapezoidal.

Combinations of the aforementioned designs are possible and occasionally mentioned in the patent literature.

The drawbacks of any of the presently known diffractive lenses can be summarized as follows:

1) Diffractive lenses or molds for diffractive lenses are difficult to machine since such lenses require exact grooves on at least one surface with groove depths in the order of microns only.
2) Due to machining imperfections—caused by the non-zero diamond tool radius—the theoretical profile cannot be machined to exactness. As a consequence, practical embodiments of such lenses exhibit a sizeable portion of non-optical surfaces. FIG. 3 compares the ideal theoretical zone profile with its corresponding practical embodiment for a lens according to the first prior art design. In FIG. 4 the comparison is for a lens made according to the second prior art design. Non-optical surfaces result in stray light, loss of in-focus light intensity and reduced contrast.
3) In ophthalmic lenses, grooves on the surface give rise to accumulation of debris, which compromises optical performance of the lens.

4) The flanks of the grooves—labeled 7 in FIG. 3 and 8, 9 in FIG. 4—which are essentially parallel or slightly inclined to the lens axis tend to reflect incoming light. Such reflected light is lost in the foci and leads to the experience of halos by the lens user.

5) Diffractive lenses—even if manufactured to near perfection—exhibit relatively high longitudinal chromatic aberration in at least one of the diffractive powers. This holds true in particular for lenses according to the first prior art design discussed above. Although some authors describe such chromatic aberration as beneficial in ophthalmic applications, the magnitude of this chromatic aberration should be maintained within certain limits, since sizably different powers for blue and red light may compromise visual resolution in the case of multi-colored objects (e.g. color prints).

6) In diffractive lenses according to the above designs, it is difficult to provide more than two main powers. Lenses with more than two main powers require peculiar zone blaze designs which are difficult to fabricate in practice.

The principal inventors of diffractive lenses of the prior art embodiments discussed above are Cohen and Freeman. The Cohen patent family encompasses in essence the following patents: U.S. Pat. Nos. 4,210,391; 4,338,005; 4,340,283; 5,054,905; 5,056,908; 5,117,306; 5,120,120; 5,121,979; 5,121,980; 5,144,483. U.S. Pat. No. 5,056,908 discloses an ophthalmic contact lens with a phase plate and a pure refractive portion within its optic zone. Freeman's patent family on diffractive lenses consists in essence of the following patents: U.S. Pat. Nos. 4,637,697; 4,642,112;4, 655,565 and 4,641,934. Still other patents on diffractive lenses were granted to e.g., Futhey (U.S. Pat. Nos. 4,830,481; 4,936,666; 5,129,718; 5,229,797), Taboury (U.S. Pat. No. 5,104,212), Isaacson (U.S. Pat. No. 5,152,788) and Simpson (U.S. Pat. No. 5,116,111). Common to all designs of the mentioned patents is the fact that optical steps are present between adjacent zones of such diffractive lenses. As a consequence, at least one of the surfaces of such diffractive lenses has a saw-toothed like profile with geometric steps.

Diffractive multifocal lenses are also disclosed in U.S. Pat. No. 5,760,871 to Kosoburd, et al. in which the geometric surface pattern is not saw-tooth, but is constructed as a periodic geometric function such as a cosine or a "super Gaussian". The '871 patent discloses that such diffractive geometric profiles are suitable for trifocal diffractive lenses, in which the intermediate power of the undiffracted light is accompanied by a $-1^{st}$ and a $+1^{st}$ diffractive order power, respectively.

As an alternative to diffractive bifocal lenses, so-called refractive bi- and/or multifocals have gained some practical importance. Such prior art lenses are either of the multiple annular zone type (FIG. 5) or are so-called aspheric designs (FIG. 6). Multi-zone refractive bifocals exhibit e.g., a far power in the odd zones 10 and a near power in the even zones 11 of the lens. The zones must not be Fresnel zones, since then such lenses would degenerate into multifocal diffractive lenses.

Refractive bi-and multifocal contact lenses are described in, e.g. M. Ruben and M. Guillon, ed. "Contact Lens Practice", Chapman & Hall Medical, London 1994, pp. 771. Typical embodiments were designed e.g. by Wesley (U.S. Pat. No. 3,794,414), de Carle (U.S. Pat. No. 4,704,016), Greendahl (U.S. Pat. No. 4,795,462), Marie (U.S. Pat. No. 5,106,180), Neefe (U.S. Pat. No. 3,560,598), Kelman (U.S. Pat. No. 4,728,182) and Tsuetaki (U.S. Pat. No. 3,431,327).

Diffraction analyses of multi-zone refractive multifocals teach that the optical path length between an object point and its conjugated image point through a zone of given refractive power is different from the optical path length between the same object and image points, if the light is refracted by another zone of identical refractive power. As a consequence, the associated light waves are not in phase in the image point, which results in reduced intensity and contrast.

In aspheric designs, the (theoretical) refractive power changes continuously from the center portion to the annular rim portion of a lens in order to focus object points at different distances into one and the same image point. The implication in such designs is that light rays through any particular position of the lens would be refracted in total independence of the other light rays through the lens. Trivially, this is not the case, and diffraction analyses explain the sometimes unexpected and usually poor performance of such lenses. In FIG. 6, an aspheric multifocal lens exhibits e.g. a spherical back surface 13 and an aspheric front surface 12. According to considerations of purely refractive optics—an approximation which does not hold true—a light ray 16 close to the lens axis would be directed into the focus 17 and a ray 14 into focus 15. Rays between the positions of rays 14 and 16 would be directed into focal points between 15 and 17.

The principal deficiency of all so-called refractive bi- and/or multifocal lenses—be it of the multi-zone or of the aspheric designs—can therefore be summarized as follows:

1) In the design of so-called refractive multifocal lenses, diffraction or light interference effects are not taken into consideration. As a consequence, waves from different portions of such lenses exhibit uncontrolled phase differences in any (multi-zone lenses) or all (aspheric lenses) of the "refractive" foci of such lenses. Uncontrolled out-of-phase vector addition of light waves leads to reduced intensity and reduced contrast in the design powers of such lenses or the absence of such design powers.

2) Since different powers are within different aperture stops (i.e. pupils), the predominant power and/or the intensity distribution between the various powers of such lenses are dependent on pupil size. For example, in aspheric designs according to FIG. 6, distance visual acuity is very poor with small pupil size (bright light) conditions.

Finally it is mentioned that designs are also known in which purely refractive powers are combined with purely diffractive powers. A contact lens may e.g. have a purely diffractive bifocal central zone which is surrounded by a purely refractive monofocal zone. Also designs are known in which a so called "refractive channel"(see U.S. Pat. No. 5,056,908 to Cohen), i.e., a purely refractive part is present within an otherwise diffractive lens. As will be appreciated, such lenses are also pupil size dependent, since the refractive portion of the lens is monofocal and the diffractive part is bifocal.

OBJECTS AND SUMMARY OF THE PRESENT INVENTION

It is an object of the present invention to provide a multifocal lens including a plurality of annular zones, and each annular zone is divided into at least two annular sub-zones such that the refractive powers within the sub-zones exhibit at least two diffractive powers and at least one of the diffractive powers substantially coincides with the average refractive power of each annular zone.

It is an object of the present invention to provide a multifocal lens which exhibits neither optical nor geometrical steps on any of its surfaces.

It is a further object of the present invention to provide a multifocal lens which essentially does not exhibit non-optical surfaces.

It is another object of the present invention to provide a multifocal lens which does not have the tendency to accumulate debris or dirt in any portion of the lens.

It is a further object of the present invention to provide a multifocal lens which does not reflect light into any non-focal position.

It is still another object of the present invention to provide a multifocal lens which has no longitudinal chromatic aberration in at least one power and only moderate longitudinal chromatic aberration in any of its other powers.

It is a particular object of the present invention to provide a multifocal lens which exhibits at least two different powers in which any of the powers can be attributed a relative intensity in independence of the relative intensity attributed to the other power.

It is another particular object of the present invention to provide a multifocal lens which exhibits at least three different powers in which any of said three powers can be attributed a relative intensity in independence of the relative intensities attributed to the other two of said three powers.

It is a still another particular object of the present invention to provide a multifocal lens in which the average phases of partial waves from different lens portions are controlled in the various powers or foci.

In accordance with one form of the present invention, a lens is divided into annular zones. Each annular zone is subdivided into at least two sub-zones. A refractive power is given to one of the sub-zones of every annular zone. The assembly or combination of the sub-zones with refractive power forms a diffractive lens having two main diffractive powers if an optical path length difference is introduced between the sub-zones. The remaining sub-zones of the annular zones are now given refractive powers such that the average refractive power of every entire annular zone is equal to one of said diffractive powers. As will be shown, one of the two principal diffractive powers of the lens is then identical with the average refractive zone power. Preferably, no optical steps are provided between any annular zones or between the sub-zones of any of said annular zones.

In another form of the present invention, a lens is divided into annular zones. Each annular zone is subdivided into at least two sub-zones. A refractive power is given to one of the sub-zones in all odd numbered annular zones, and a refractive power is given to one of the sub-zones in all even numbered annular zones. Then the assembly or combination of said sub-zones with refractive power forms a diffractive lens with two main diffractive powers if optical path lengths differences are introduced between the odd and the even sub-zones. The remaining sub-zones of all odd and even annular zones are given refractive powers such that the average refractive powers of the odd annular zones are equal to one of the main diffractive powers, and the sub-zones of all even annular zones are given refractive powers such that the average refractive powers of the even annular zones are equal to the other of the main diffractive powers. As a consequence, both of the main diffractive powers of the lens are at the same time refractive powers of the lens. Preferably, no optical steps are provided between any zones or sub-zones of the lens.

In a still further form of the invention, a multifocal lens exhibiting at least two principal lens powers $D_1$ and $D_2$ includes a plurality of annular zones. Preferably, there are no geometric or optical steps between the annular zones. Each annular zone j is subdivided into at least two annular sub-zones, i.e., a main sub-zone and a phase sub-zone. Preferably, there are no geometric or optical steps between the main sub-zones and the phase sub-zones. Each main sub-zone of the annular zone j exhibits a refractive power $D_{j,G}$ and each phase sub-zone of the annular zone j exhibits a refractive power $D_{j,S}$. Each annular zone j exhibits an average refractive power $D_{1,j}=D_{j,G}((1-p_j)+D_{j,S} \times p_j$, wherein $p_j$ is the fraction of the phase sub-zone of the entire annular zone j. The average refractive power $D_{1j}$ includes a first principal zone power. Additionally, each annular zone j exhibits an inner bonding radius $r_{j-1}$ and an outer bonding radius $r_j$, such that the bonding radii provides a power difference $\Delta D_j=2\lambda/(r_j^2-r_{j-1}^2)$ of the annular zone j, wherein $\lambda$ is a design wavelength. A second principal zone power $D_{2j}$ is given by $D_{2j}=D_{1j} \pm \Delta D_j$, such that the principal lens power $D_1$ is the average of the principal zones powers $D_{1j}$, and the principal lens power $D_2$ is the average of the principal zone powers $D_{2j}$.

In a preferred embodiment, the annular zones of a lens according to the present invention exhibit equal areas. The sub-zones of a lens according to the present invention may exhibit different areas in different annular zones. The design parameters for the lens are equally applicable to manufacturing multifocal mirrors.

Still other forms of the present inventions will be discussed in the following detailed description of preferred embodiments.

BRIEF DESCRIPTION OF THE DRAWINGS

FIG. 8 shows the through focus response of a lens formed in accordance with the present invention for three different visual wavelengths.

FIG. 9 shows the through focus response of another lens formed in accordance with the present invention.

FIG. 11 shows the through focus response of a trifocal lens formed in accordance with the present invention exhibiting arbitrary intensities in the three powers.

DETAILED DESCRIPTION OF THE PREFERRED EMBODIMENTS

Figure 1:
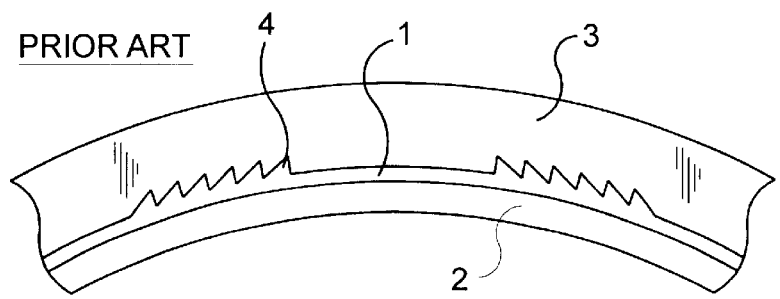
FIG. 1 is a schematic view of the center portion of a prior art diffractive multifocal contact lens according to one known design.
Figure 2:
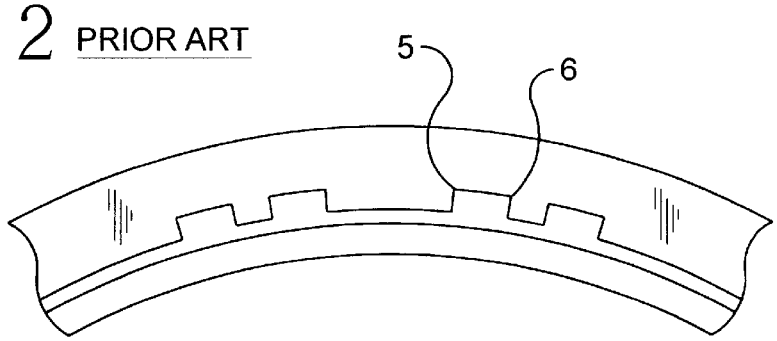
FIG. 2 is a schematic view of the center portion of a prior art diffractive multifocal contact lens according to another known design.
Figure 3:
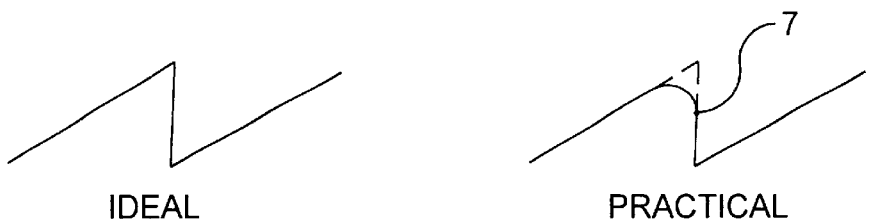
FIG. 3 compares the ideal zone blaze of a prior art diffractive lens according to a known design with the corresponding practical machined zone blaze.
Figure 4:
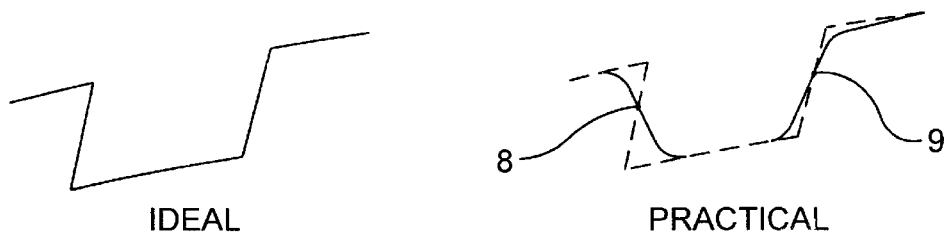
FIG. 4 compares another ideal zone blaze of a prior art diffractive lens according to another known design with the corresponding practical machined zone blaze.
Figure 5:
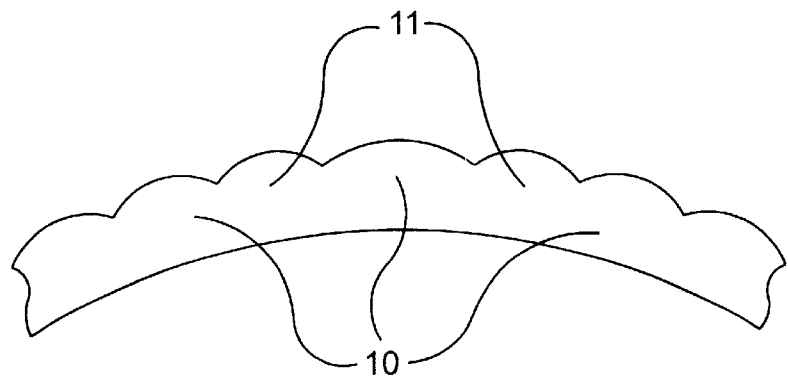
FIG. 5 is a schematic view of the inner portion of a prior art multizone refractive bifocal lens.
Figure 6:
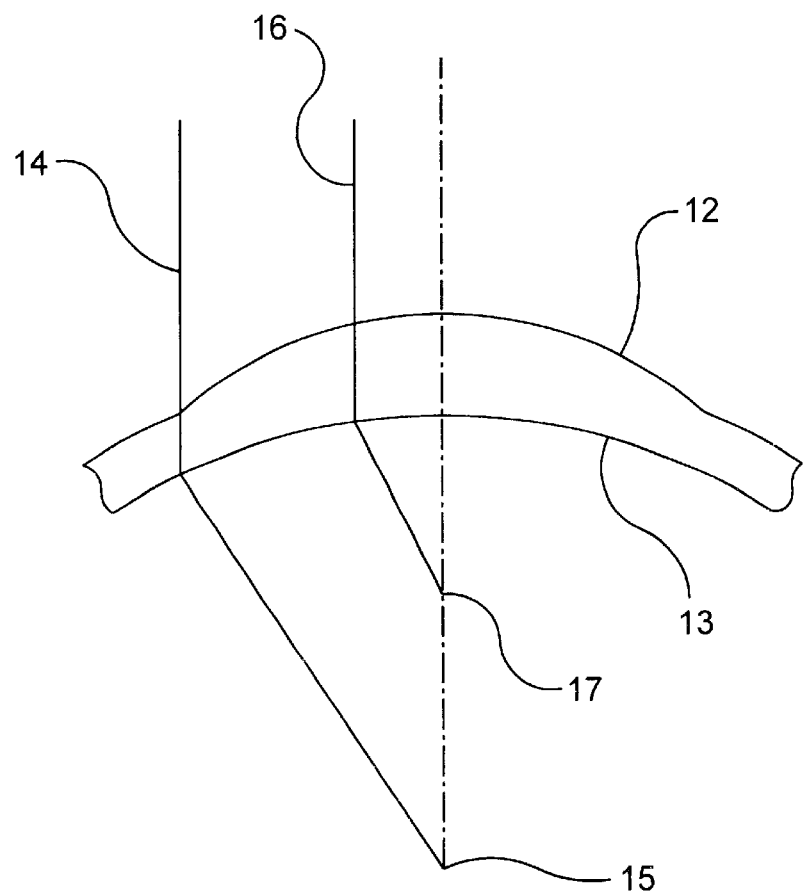
FIG. 6 is a schematic view of a prior art refractive aspheric multifocal lens.

According to the present invention, a lens is divided into any number of annular lens zones. Contrary to e.g. state of the art refractive multizone multifocal lenses, the zones are chosen to exhibit equal areas, i.e. they are Fresnel or annular zones. Also contrary to state of the art multifocal diffraction lenses, no optical or geometrical steps are provided between any two adjacent lens zones.

According to the present invention, any of the Fresnel or annular zones is subdivided into at least two annular sub-zones. By way of example (FIG. 7) we discuss the case where the zone is divided into two annular sub-zones 18 and 19. Sub-zone 19, which is the smaller zone, covers a fraction p of the entire zone area; then the other sub-zone 18 covers a fraction (1−p) of the entire zone area. The larger sub-zones are given a refractive power $D_G$, and the smaller sub-zones are given a refractive power $D_S \neq D_G$, as a consequence, the sub-zone front radii 20 and 21 are different whereas the sub-zone back radii 22 and 23 may be equal; or vice versa. The assembly or combination of the larger sub-zones 18 wherein each sub-zone 18 exhibits the refractive power $D_G$, represents a multifocal diffractive lens. In such a design, phase differences are introduced between consecutive larger sub-zones 18 by the smaller sub-zones 19 which exhibit the power $D_S \neq D_G$. The difference $\Delta D$ between the powers of this diffractive lens is given by the following equation:

$$\Delta D = \frac{8\lambda N}{B^2} \quad (1)$$

where $\lambda$ is a design wavelength, N is the number of Fresnel or annular zones and B is the diameter of the lens (see J. W. Goodman, Introduction to Fourier Optics, McGraw-Hill, San Francisco 1968, p. 125)

If the wavelength difference between consecutive sub-zones 18 is $\lambda/2$, the two main diffractive powers have the values $D_1 = D_G - \Delta D/2$ and $D_2 = D_G + \Delta D/2$.

According to this invention, the smaller sub-zones are given a refractive power $D_S$ such that the average refractive power $D_{av}$ of the entire Fresnel zones is equal to. one of the diffractive powers $D_1$ or $D_2$, i.e.

$$D_{av} = D_G(1-p) + D_S \times p = D_G \pm \frac{\Delta D}{2} \quad \text{and} \quad (2)$$

$$D_S = D_G \pm \frac{\Delta D}{2p} \quad (3)$$

As a first practical example we consider a lens which should exhibit the main powers $D_1=1$ diopter and $D_2=3$ diopters. Then $\Delta D=2$ diopters and $D_G$ has to be 2 diopters. For a power difference $\Delta D=2$ diopters we need e.g. 16 Fresnel zones on a 5.93 mm diameter, if the design wavelength is chosen to be 550 nm. By way of example, the percentage of the smaller sub-zone should be 20.%, i.e. p=0.2, and the average refractive zone power should be the smaller of the two powers, i.e. 1 diopter. With equation 3 we get for the power in the smaller zone—which will be referenced herein as the "phase sub-zone"—the value $D_S=-3$ diopters.

FIG. 8 illustrates the through focus response (TFR) of this lens example. As can be seen, the principal powers for light of 550 nm are 1 and 3 diopters. The phase sub-zones with refractive power −3 diopters provides for a $\lambda/2$ optical path length difference between the larger sub-zones which exhibit the power 2 diopters. In a "normal" diffractive lens, the two intensity peaks would be equally high (40.5%) for such an optical path length difference. By contrast, the present lens exhibits 57.2% relative peak intensity in the power of 1 diopter (zeroth order diffractive power) and 25.9% in the power of 3 diopters (first order diffractive power). This is due to the fact that the zeroth order diffractive power and the refractive power of all zones are intrinsically combined in the power of 1 diopter. As can be seen from FIG. 8, the power which at the same time is a diffractive and a refractive power is free of longitudinal chromatic aberration, i.e. it is, as mentioned, the zeroth order diffractive power. In this example, the other power of 3 diopters is a purely diffractive power and shows the known longitudinal chromatic aberration. Mind that altogether 57.2%+25.9%=83.1% intensity are present in the main powers, which is more than the 81% (40.5%+40.5%) in a normal diffractive lens with $\lambda/2$ optical steps between zones.

According to this invention, the phase shifts between partial waves from different portions or zones of the lens, which phase shifts are required for multifocal performance, are not provided by e.g. optical steps like in diffractive lenses but by "phase sub-zones" with appropriate refractive power. Further on, the refractive powers of the phase sub-zones are chosen such that the average refractive powers of the entire zones are equal to at least one of the diffractive powers of the total zoned lens assembly. In replacing the optical and geometrical steps by sub-zones of refractive power, the outer surface of this multifocal lens is kept smooth. Still, the lens cannot be considered solely a diffractive lens, since, intrinsically, at least one power is at the same time a diffractive and an average refractive power.

For the sake of completeness it is mentioned that according to the present invention the average zone power Day can also be given the value of any higher order n diffractive power, i.e.

$$D_{av} = D_G(1-p) + D_S \times p = D_G - \frac{\Delta D}{2} \pm n \times \Delta D \quad (4)$$

from which equation the value for $D_S$ can be calculated. Such lenses tend to have high longitudinal chromatic aberration in their main diffractive powers. This may be a desired feature for certain applications.

The relative intensity distribution over the main powers of the lens according to FIG. 8 may not be a desired distribution. It will be shown how an arbitrary distribution of peak intensities over two desired powers can be achieved:

It is known that the positions and relative intensities of the main diffractive peaks of a diffractive lens can be changed by altering the optical step height between the zones of the diffractive lens. Similarly, the value $\Delta D/2$ in equation (2) can be replaced by the general expression $\Delta D^*z$, where z is a value between e.g. −1 and +1. In the design, the lens should exhibit two main powers $D_1$ and $D_2$. Introducing the average power, $D_m = (D_1 + D_2)/2$ the required refractive power $D_G$ of the main sub-zones can be expressed as follows:

$$D_G = D_m \pm \Delta D \times (\frac{1}{2} - z)$$

and the refractive power of the phase sub-zone can be expressed as follows:

$$D_S = D_G \pm \frac{\Delta D}{p} z \qquad (6)$$

In the above equations the "+" sign applies to the case where the average refractive power is equal to the larger of the two powers. (see below "type B" zone). The "−" sign applies to the cases where the average refractive power is equal to the smaller of the two powers (see below "type A" zone).

By changing the value of z we get different values for $D_G$ and $D_S$ in the lens according to this invention, while $D_1$ and $D_2$ remain unaltered. The relative intensities in the powers $D_1$ and $D_2$ will change with changing values for z or $D_G$ and $D_S$, respectively. Thus, the desired relative intensities in the two powers can be preset and the corresponding value for z calculated. This calculation is usually being done by applications of trial and error methods.

As can be seen from equations (5) and (6), $D_S$ and $D_G$ are identical for z=0. Then, no phase shift exists between different annular zones or annular sub-zones. Thus, it can be concluded that the value of z is a measure of the phase shift between light emerging from two main sub-zones of adjacent annular zones.

It should be understood that the total phase shift $z_t$ of light between two main sub-zones may also be composed of a partial phase shift z which is provided by a phase sub-zone and another phase shift $z_s$ which—in analogy with a diffractive lens—is provided by an optical step; then $z_t=z+z_s$. Such an optical step $z_s$ may be introduced between the main sub-zone and the phase sub-zone of any given annular zone as well as between the phase sub-zone of any annular zone and the main sub-zone of the adjacent annular zone. Such a lens would essentially represent a diffractive lens in which the required phase shift between adjacent annular zones is not exclusively provided by optical or geometric steps, but also by appropriate refractive powers within fractions (i.e. the phase sub-zones) of the annular zones.

The following discussion will focus on the case where the phase shifts are provided exclusively by phase sub-zones. However, to one knowledgeable in the art, it will be understood that phase shifts can be provided through the introduction of optical steps between any given zone as discussed above.

By way of example, a lens exhibiting an achromatic power of −1 diopter and an additional power of 1.5 diopter is considered. In the achromatic power of −1 diopters we want 40% (+/−2%) relative peak intensity, and in the 1.5 diopter power the remaining 60% (−/+2%) relative peak intensity.

According to the above guidelines, such a lens would have to exhibit e.g. 22 Fresnel zones on a 6.223 mm diameter (design wavelength: 550 nm). If we chose the value p=0.15 for the fraction of the phase sub-zone in all Fresnel zones we get the following results: $D_G$=0.65 diopters, $D_S$=−10.33 diopters and z=0.66. As can be shown, there are more than one solution for z (and $D_G$ and $D_S$) if we allow for an error margin, as indicated above, but the maximum total intensity in the two powers is for z=0.66.

In FIG. 9 the TFR for the lens of this example is shown. Let us assume that the present lens is a contact lens with back radius 8 mm and center thickness 0.2 mm. Let us further assume that the lens is made from a material of refractive index 1.49. The lens should have a uniform back surface; therefore the front surface main and phase sub-zones which carry-different powers will exhibit different front radii. In our example, the front radii of the main sub-zones with 0.65 diopters refractive power will be close to 8 mm. The front radii of the phase sub-zones are approximately 9.3 to 9.6 mm. As will be appreciated, such a lens front surface is smooth and without any geometric or optical steps.

Contact lenses formed in accordance with the embodiment of the present invention discussed above have been manufactured and demonstrate the expected performance. In particular, the tear film did not rupture, even when the varying radii of the main sub-zones and phase sub-zones were placed on the front surface of the lens.

Naturally, it is also possible to design a lens according to the present invention with a segmented smooth back surface having different radii in different sub-zones as well. Particularly suitable for contact lenses with back surface optics are lenses in which even and odd zones, respectively, are given different average powers (see below). Lenses according to the optical design discussed so far would exhibit a smooth back surface with no geometric or optical steps, but there would be back surfaces of sub-zones with rather small radii on the enveloping surface which enveloping surface is the corneal surface. Still other lens designs according to this invention are preferred, if the lens optics is to be put on the back surface of a contact lens (see below).

As an important principal feature, the value for p (i.e. the fraction of the phase sub-zone with respect to the entire Fresnel zone) does not need to be the same in all Fresnel zones of the lens. This means that the power profiles of the Fresnel zones are not necessarily periodic in $r^2$-space. Since the width of the inner Fresnel zones is smaller than the width of the outer Fresnel zones, it can be advantageous to have smaller values for p in the inner zones and larger values for p in the outer zones. The function for the increase (or decrease) of p with increasing zone number is also arbitrary. With this it is equally possible to find the appropriate value for z according to above equations (4) and (5).

Figure 7:
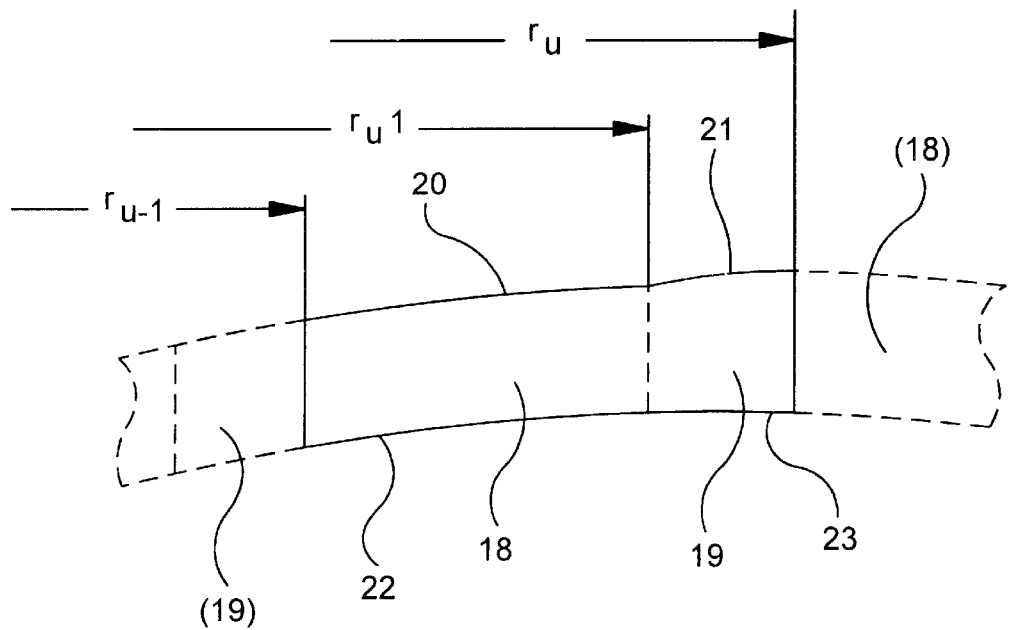
FIG. 7 is a schematic view of a lens zone of a lens found in accordance with the present invention.
Figure 10:
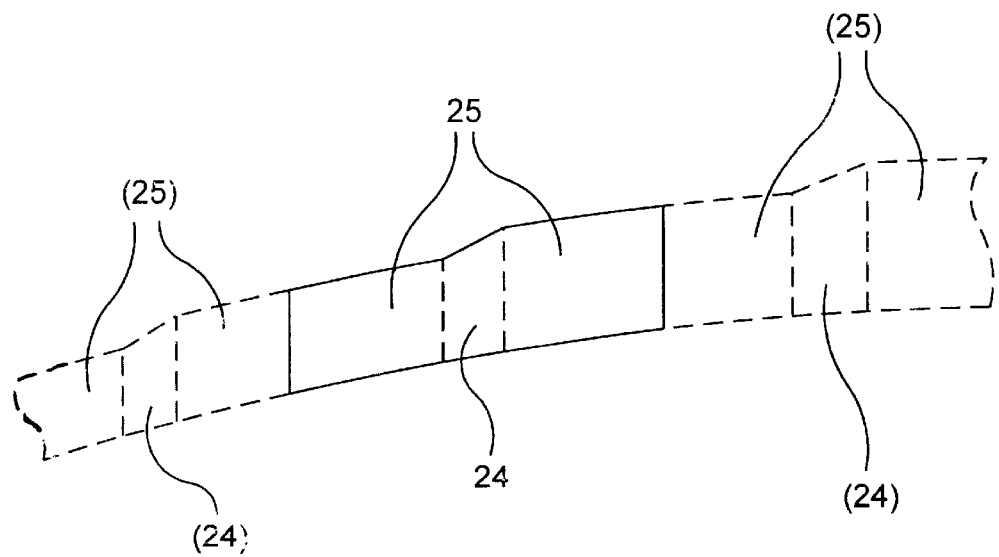
FIG. 10 is a schematic view of another embodiment of a lens zone of a lens formed in accordance with the present invention

It is further mentioned that the phase sub-zone does not need to be positioned at the rim of the Fresnel zone, as drawn e.g. in FIG. 7. Instead, it can be located in any annular position within the Fresnel zone without changing the general performance of the entire lens. Such a design can be advantageous in the case of lenses in which the desired difference between the main powers is small. Such lenses, as will be appreciated, will have a rather large central Fresnel zone. In the case of an ophthalmic lens, a very small pupil may then cover only the central zone or just very few of the inner zones. Positioning the phase sub-zone closer to the lens center in the individual Fresnel zones can then improve bi- or multifocal lens performance. FIG. 10 is a schematic view of a Fresnel zone in which the phase sub-zone 24 is positioned in the middle of said Fresnel zone and not at the rim of said Fresnel zone, like e.g. in FIG. 7. The main sub-zone 25 of the entire Fresnel zone consists now of two parts. In embodiments where the main sub-zone carries only one refractive power (see below), both of these parts exhibit the same refractive power.

Finally it is mentioned that with decreasing value for z the relative intensity in the power which is a combination of a diffractive and a refractive power increases. In the case where z=0 we get $$D_G = D_S = D_m \pm \frac{\Delta D}{2} \qquad (7)$$

i.e., we have a monofocal lens of either power $D_1$ or $D_2$ with 100% relative intensity in the then only existing purely refractive power $D_G$. From these considerations it will be apparent that a change of the value z is accompanied by a change of the values for the relative peak intensities in the available powers $D_1$ and $D_2$.

According to the present invention, the required phase differences for light waves from different annular lens zones are provided by appropriate phase sub-zones within said annular zones. In more general terms, it can be said that appropriate power profiles within the Fresnel zones are required. In embodiments according to FIG. 7 this power profile $D_z(r)$ within the considered Fresnel zone can be described as follows:

$$D_z(r) = \begin{matrix} D_G & \text{for } r_{n-1} \le r < r_n' \\ D_S & \text{for } r_{n'} \le r < r_n \end{matrix} \qquad (8)$$

In equation (8) $r_{n-1}$ refers to the inner bonding radius of the n-th Fresnel zone, $r_n$ refers to the outer bonding radius of the larger of the two sub-zones within the entire Fresnel zone, and $r_n$ is the outer bonding radius of the Fresnel and at the same time the outer bonding radius of the phase sub-zone.

In the examples discussed so far, the power profiles $D_2(r)$ within the Fresnel zones were discontinuous. But, as will be appreciated, also continuous power profiles will provide the required phase differences in multifocal lenses with annular zones.

In general, the uniform powers $D_G$ and $D_S$ in any Fresnel zone have to be replaced by expressions for average powers of the following kind:

$$D_G = \frac{\int_{r_{n-1}}^{r_n'} rD_z(r)dr}{\int_{r_{n-1}}^{r_n'} rdr} \quad \text{and} \quad D_S = \frac{\int_{r_{n'}}^{r_n} rD_z(r)dr}{\int_{r_{n'}}^{r_n} rdr}$$

The proper choice of a continuous zone power profile will depend on the choice of the radii 22 and 23 of the other bonding lens zone surface, on the index of refraction of the material used in lens fabrication and, indirectly, on the choice of the parameters p in the individual Fresnel zones, which, as was already mentioned, are not necessarily equal in all zones.

In view of modem computation tools, a continuous power profile will be approximated by a discontinuous power profile to any degree of exactness rather than calculated analytically. For this end the two sub-zones will be further subdivided into any number m of partial sub-zones and the individual powers in the sub-zones be weighted with the areas of the sub-zones. Systematic variation of the m discrete powers in the partial sub-zones allows to find the suitable powers $D_{G,1}, D_{G,2} \ldots D_{G,k}$ and $D_{S,k+1} \ldots D_{S,m}$ for the desired performance of the multifocal lens according to this invention. The objective function of such trials will likely be maximum total intensity in the two (or more, see below) desired powers. By increasing the number m of partial sub-zones, a continuous power profile can be approximated to any desired degree of exactness. The power profile of the entire Fresnel zone which consists of the power profile in the main sub-zone and the power profile in the phase sub-zone is not necessarily periodic in $r^2$-space, since, as mentioned above, the fraction p of the phase sub-zone can be different in different Fresnel zones. Numerical studies have shown that best results are obtained for uniform powers $D_G$ in the main sub-zones, i.e. $D_{G,1}=D_{G,2}=D_{G,k}=D_G$. Also, it was found that a uniform power $D_S$ in any of the phase sub-zones results in peak intensities in the desired lens powers which are close to the intensities with optimized power profiles in any of the phase sub-zones. These results are important for practical lens design.

In view of the above and since it is sufficient for the explanation of the principles of the present invention, lenses are discussed herein which the Fresnel zones are subdivided into just two sub-zones, a main sub-zone and a phase sub-zone. But as will be appreciated by those skilled in the art, lenses with more than two sub-zones in their individual zones as well as lenses with a continuous power profile in said individual zones do not depart from the scope or spirit of the present invention.

In the lenses according to this invention discussed so far, one of two main powers was purely diffractive, the other was both a diffractive and a refractive power. But, as will be shown, it is possible also, to design a lens in such a way that not only one, but at least two main powers are intrinsically both diffractive and refractive powers.

Calling again the main powers $D_1$ and $D_2$ with $D_2>D_1$, we need two average refractive powers in two kinds of zones. It is then practical to distinguish between odd and even Fresnel zones and give e.g. the average refractive power $D_1$ to the odd zones and the power $D_2$ to the even zones. The number of required zones N on a lens of diameter B is again governed by equation 1 in which $\Delta D=D_2-D_1$. Introducing again the average power $D_m=(D_1+D_2)/2$, we can derive the following relations:

$$D_{G,o}=D_m-\Delta D \times (½-z_o) \qquad (5')$$

$$D_{G,e}=D_m+\Delta D \times (½-z_e) \qquad (5'')$$

$$D_{S,o} = D_{G,o} - \frac{\Delta D}{p_o}z_o \qquad (6')$$

$$D_{S,e} = D_{G,e} + \frac{\Delta D}{p_e}z_e \qquad (6'')$$

In the above equations the added sub-scripts "o" and "e" refer to "odd" and "even" zones. For example, $D_{G,o}$ refers to the refractive power in the major or main sub-zone of the odd Fresnel zones, and so on. In lenses with practically continuous power profiles in the sub-zones the values $D_{G,o}$, $D_{G,e}$, $D_{S,e}$, and $D_{S,e}$, respectively, are average values, as explained above.

As can be verified, the average refractive power of the odd zones results in $$D_{av,o} = (1 - p_o) \times D_{G,o} + p_o \times D_{S,o} = \ldots = D_m - \frac{\Delta D}{2} \qquad (9)$$

By the same argument, the average refractive power of the even zones is given by $$D_{av,e} = D_m + \frac{\Delta D}{2} \qquad (9')$$

and finally, the average power of all zones, i.e. of odd and even zones is $$D_{av,all}=D_m \qquad (10)$$

Again, the fractions $p_o$ and $p_e$ of the phase sub-zones in the odd and even Fresnel zones may be different in different zones. Also the position of the phase sub-zone within the Fresnel zone can be arbitrary.

The set of equations (5') to (6") indicates that with given values for $D_m$, $\Delta D$, and with any set of parameters $p_o$ and $p_e$ (which can be different in different Fresnel zones as earlier mentioned), the refractive powers of the individual sub-zones are solely functions of $z_o$ and $z_e$. Since the relative peak intensities in the powers $D_1$, $D_m$ and $D_2$ depend on the values $z_o$ and $z_e$, practically any relative intensity distribution over the three powers $D_1$, $D_m$ and $D_2$ can be obtained by a proper choice of values for $z_o$ and $z_e$. Trial and error methods involving variations of $p_o$ and $p_e$ in different Fresnel zones lead to the computation of adequate values for $z_o$ and $z_e$.

By way of example we consider a lens which should be trifocal and exhibit the main powers −1, 0.25 and 1.5 diopters. Such a lens requires e.g. 24 Fresnel zones on a 6.5 mm diameter. By way of example, the relative intensities I(D) in these powers should be of the following ratio: I(−1): I(0.25): I(1.5)=100:80:90 within an error margin of 2%. Further, we assume that $p_o$ in the first zone is 0.10 and $p_e$ in the outermost $24^{th}$ zone is 0.20. By way of example, all $p_o$'s and $p_e$'s for the intermediate zones are linearly interpolated. As can be shown, more than one combination of values for $z_o$ and $z_e$ exist with which the above condition for the three relative intensities is satisfied. Maximum total intensity I(−1)+I(0.25)+I(1.5) is achieved for the values $z_o$=0.28 and $z_e$=0.33. FIG. 11 shows the through focus response, TFR, for this lens. The intensity distribution for both the design wavelength 550 nm and for polychromatic light (Gaussian with 20% of peak intensity (at 550 nm) in both 450 and 650 nm). It will be appreciated that the broadening of the peaks in the power of 1 and +1.5 diopters, respectively, is due to longitudinal chromatic aberration (see FIG. 8 for comparison).

For the design wavelength, the total in-focus intensity is over 86% with the present choice of parameters; this percentage can be increased if other (usually smaller) values for the $p_o$'s and $p_e$'s are chosen, and if the phase sub-zones are still further divided into a series of smaller annular zones, as discussed above. For polychromatic light, the peaks are broadened in the powers of −1and +1.5 diopters, indicating longitudinal chromatic aberration of this lens. This chromatic aberration is moderate, when compared to the values for the longitudinal chromatic aberration of typical multi-focal diffractive lenses.

For some applications it may be advantageous to attribute a certain refractive power $D_{G,f}$ to one or more of the main sub-zones which refractive power is different from the value $D_G$ of equation (5) of above. Then the following equation must hold:

$$D_{G,f} = D_m \pm \Delta D \times (\tfrac{1}{2} - z_f) \quad (5''')$$

where $z_f$ differs from the value z of equation (5). Combining equations (5) and (5''') results in $$z_f = z \pm \frac{D_G - D_{G,f}}{\Delta D}$$

and the corresponding refractive power $D_{S,f}$ of the adjacent phase sub-zone assumes the value $$D_{S,f} = D_{G,f} \pm \frac{\Delta D}{p} z_f \quad (6''')$$

As an example, it may, in particular, be advantageous to attribute the larger power $D_2$ of the two principal powers of a bifocal lens to one or more of the main sub-zones, while the average refractive power of the entire Fresnel zone (consisting of the main sub-zone and the phase sub-zone) should still be equal to the smaller power $D_1$ of the two principal powers. With $D_m=(D_1+D_2)/2$ and $\Delta D=(D_2-D_1)$ the above equations yield the solutions $$z_f = 1$$

and $$D_{S,f} = D_{G,f} \pm \frac{\Delta D}{p}.$$

As a particular example, a bifocal lens exhibiting the two principal powers 1 diopter and 3.5 diopters is considered. This lens should consist exclusively of "type A" zones, and the main sub-zones should exhibit the refractive power 3.5 diopters. All phase sub-zones should cover 25% of the entire Fresnel zones, i.e. p=0.25. With these assumptions, the following values for the various refractive powers are obtained: $D_{G,f}$=3.5 diopters, $D_{S,f}$=−6.5 diopters, $D_1$=1 diopter, and $D_2$=3.5 diopters. The power $D_2$ is the first order diffractive power, the power $D_1$ is both the zeroth order diffractive power and the average refractive power of the lens.

Figure 12:
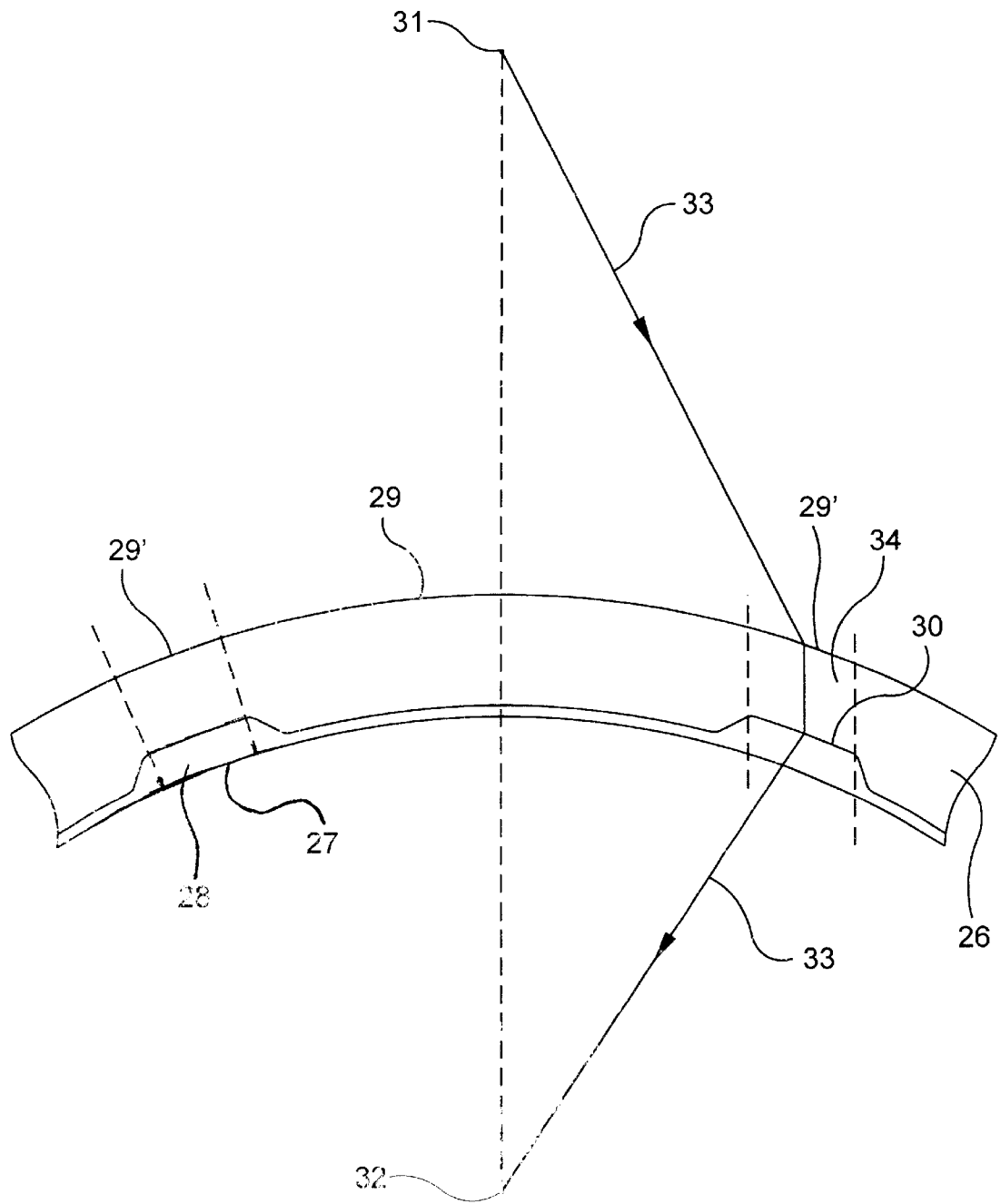
FIG. 12 is a schematic view of a portion of a lens design formed in accordance with the present invention.

The present invention refers to lenses with annular zones in which the annular zones exhibit the refractive powers according to equations (2), (3), (5), (6) and/or (5') through (5' ) and/or (6') through (6'''). Also, as earlier explained, the powers of the sub-zones $D_G$ and $D_S$, respectively, may be average powers. In principle, it is arbitrary, whether the zones or sub-zones exhibit front or back surface optics in order to satisfy the conditions according to the mentioned restrictions. Mention is made, though, that lens designs in which the odd and even zones exhibit different average refractive powers are particularly suitable for contact lenses in which the required zone or sub-zone power profiles are provided by zones or sub-zones which exhibit adequate curvatures or radii on the back surface which, in the case of a contact lens, is adjacent to the cornea. FIG. 12 is a schematic sketch of the central part of such a lens. When the refractive powers in the main sub-zones of the annular zone lenses are chosen to be uniform, approximately 40% of the central optic part of the lens surface exhibit a back surface which can be shaped such that it is complementary to the corneal surface, thus providing optimum lens comfort.

FIG. 12 shows the inner optical part of a lens 26 which is dimensioned such that it is suited to rest on a cornea 27 of given radius. The front surface 29 is smooth, although not necessarily purely spherical, if the required phase relations of such a lens are to be satisfied to a high level of exactness. Should the phase relations be satisfied to a high level of exactness, the front surfaces of the individual sub-zones will be individual spherical surfaces 29' and the entire front surface 29 will be a multi-curve consisting of spherical portions 29' (see FIG. 12). In the calculations of adequate lens zone parameters, like the individual intermediate radii of curvature 30, the refractive powers of the tear lenses 28 has to be duly taken into consideration. Illustrating the general dimensioning and designing method for such lenses, let us assume that the annular sub-lens 34—which is bounded by the two dotted lines in FIG. 12—has to exhibit a certain refractive power D. Then, as will be understood, an object point 31 and its conjugated image point 32 can be defined. A light ray originating in 31 must then be refracted by the sub-zone lens such that it arrives in 32. The front surface 29 and the back surface 27 of sub-zone lens 34 are given, and also the refractive lens index between surfaces 29 and 30 and the refractive index of the optical medium between surfaces 30 and 27, respectively, are known; in the case of a contact lens made of given single lens material this optical medium will be the tear fluid.

It will be appreciated that by variation of the position and inclination of the spherical surface element 30 an embodiment of sub-zone 34 can be found such that a light ray 33 originating in object point 31 is indeed directed into the conjugated image point 32. Mention is made that phase relations between zones or sub-zones do not need to be taken into consideration separately, since there are no optical steps between any of the zones or sub-zones. Consequently, once the required refractive powers within all zones or sub-zones are established (see above equations), lens dimensioning can be executed in a straightforward manner according to the above guidelines. All that matters for lenses according to the present invention is the correct sequence of geometric powers in main and phase sub-zones, $D_G$ and $D_S$, respectively. Whether these main and phase sub-zones exhibit front or back surface optics is a matter of design choice.

As will be understood, in the case of a lens with back surface optics, not only can tear fluid be employed, but any lens material which exhibits a refractive index other than the index of the base lens material can be used. Then the back surface of this composite lens is given by the surface 27 of FIG. 12. In the case of a contact lens, this surface 27 will be shaped complementarily to the corneal surface. Lens dimensioning will follow exactly the rules discussed in connection with lenses according to FIG. 12.

To one knowledgeable in the art, it will be clear how to apply the above discussed general dimensioning routines for the individual sub-zones to lenses of any of the discussed designs with a smooth front surface and continuous back surfaces within the individual sub-zones, i.e. to lenses with back surface optics. Since in lens designs discussed at the beginning of the paragraph only a small percentage of the entire back surface would rest on the cornea, it may be advantageous to use a solid or elastic lens material in the minute spacings between the base lens 26 and the back bonding surface—surface 27 of FIG. 12—instead of the tear fluid.

Back surface optics test lenses with geometric powers $D_G$ and $D_S$ according to the above equations (5) and (6) were fabricated and successfully tested. These lenses were made from soft lens buttons and thus consisted of a single material. Beyond expectations, lens comfort was excellent, even in circumstances in which the cornea was covered by a rather small fraction of the lens back surface only. In one version, the simultaneous diffractive and refractive power was the smaller of the two main lens powers (minus-sign in equations (5) and (6)). For the sake of simplicity, this lens design is hereinafter referenced to as "type A" lens, since this lens consists of "type A" zones only. In another version, the simultaneous diffractive and refractive power was the larger of the two main lens powers (plus sign in equations (5) and (6)). This design will be hereinafter referred to as a "type B" lens, since this lens consists of "type B" zones only. As mentioned above, the lens power which is created by the combination of refractive and diffractive powers, is free of longitudinal chromatic aberration.

In view of the above disclosure, it will be understood that type A lenses exhibit no chromatic aberration in the far power and chromatic aberration in the near power. For type B lenses, the situation is reversed. By combining type A and type B zones into a single lens, the chromatic aberration can be distributed over the main powers of the resulting lens in an almost arbitrary fashion. For example, if a combination of two type A Fresnel zones is followed by one type B Fresnel zone, one third of the total chromatic aberration will be manifest in the far power and two thirds of the total chromatic aberration in the near power. A combination of three type A with two type B Fresnel zones will yield a lens in which two-fifths of the total chromatic aberration is manifest in the far power and three-fifths in the near power, etc.

Figure 13:
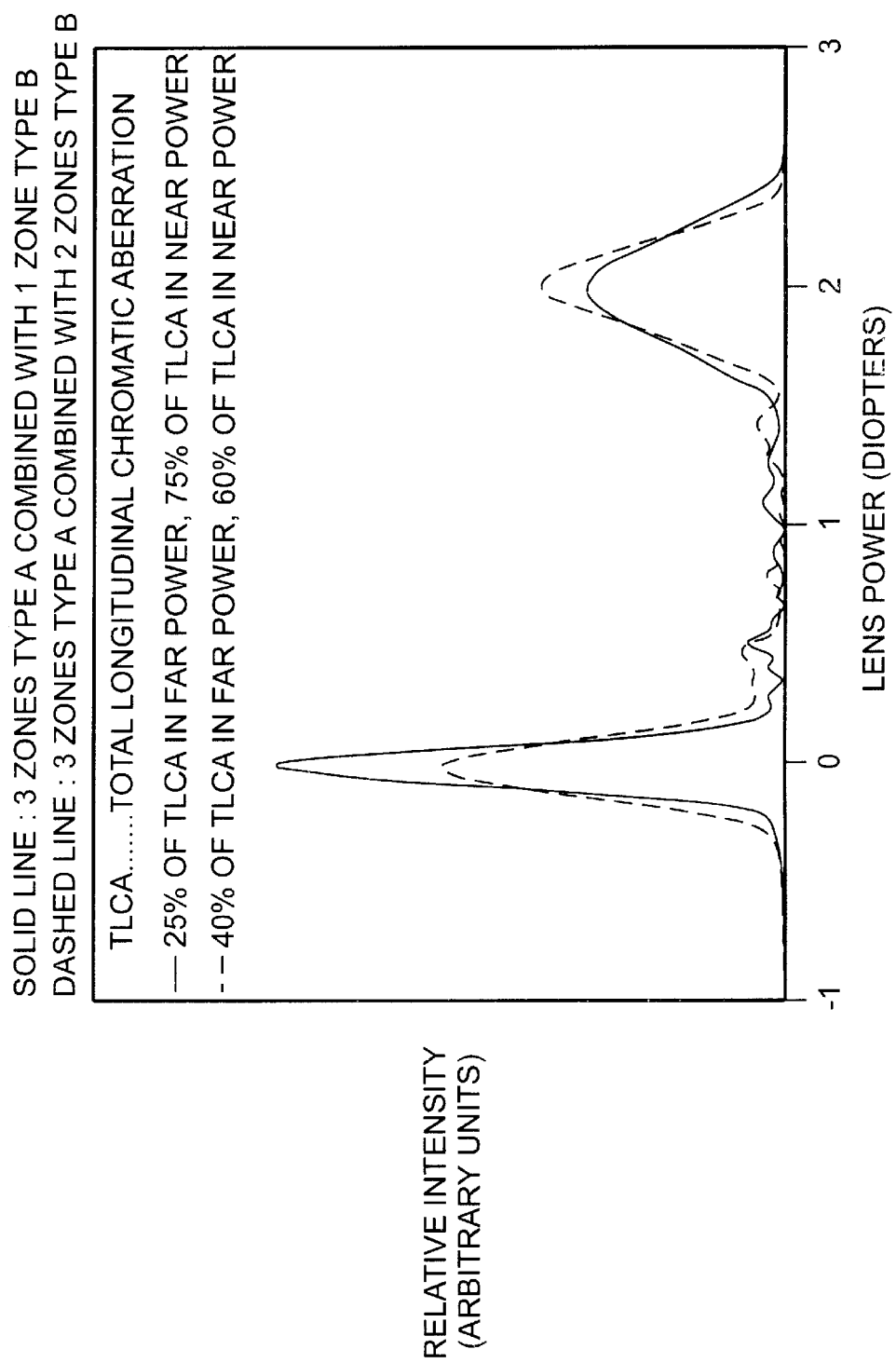
FIG. 13 shows the through focus response for two bifocal lenses according to this invention.

Generally, if m zones of type A are combined with n zones of type B, the longitudinal chromatic aberration in the lower power will be a fraction n/(n+m) of the total longitudinal chromatic aberration, and, in the higher power the comparable fraction will be m/(n+m). Also, as will be understood, the signs of the partial chromatic aberrations in the two powers will be opposite. FIG. 13 shows the TFRs of two different lenses with two different distributions of chromatic aberration in two main powers.

A lens found in accordance with the present invention exhibits refractive powers within individual annular sub-zones which are generally different from the principal lens powers. The refractive powers of the phase sub-zones (see above) are always different from the principal lens powers. Mind that in the first example of this disclosure (TFR in FIG. 8), the principal lens powers were +1 and +3 diopters, whereas the power of the phase sub-zones was −3 diopters. Also, it is further disclosed that in the lens example of FIG. 11, in which the principal powers were—1.00, 0.25 and 1.50 diopters, the refractive powers of the first eight innermost sub-zones are e.g.: −0.3, −7.3, +0.675, +8.581, −0.3, −6.74, +0.675, +7.973 . . . diopt Clearly, these refractive powers show no apparent correlation with the resulting lens powers. It should also be noted that in this type of lens, the refractive powers decrease and increase in a rather—but not strictly periodic fashion.

With modern lens power mapping apparatus it is possible to determine the local refractive powers in very small annular zones. Such measurements can therefore identify a lens made in accordance with the present invention. Such an identification is made easier if in addition to the local refractive powers the relative sizes (areas) of the individual annular zones are also determined: In our example the first two sub-zones would exhibit the relative sizes 90% (first zone) and 10% (second zone sizes $(1-p_o)$=90% (First main sub-zone) and $p_o$=10% (first phase sub-zone) with this the average power is −0.3×(0.9) −7.3×(0.1)=−1.00 D which—in agreement with the general theory of lenses according to this invention—is the smallest of the three principal powers of this lens. According to the choice of the parameters $p_o$ and $p_e$ for the lens of FIG. 11; the value $p_e$ in the second annular zone is 10.435%. With this, the average refractive power in the second annular zone is $0.675×(1-p_e)+8.581×p_e=1.5$ diopters which is the largest of the main powers of the lens. And, as can easily be verified, the average refractive power of the first and second annular zones is 0.25 diopters which is the intermediate of the lens main powers.

All lenses discussed so far comprise annular zones which all exhibit equal areas, i.e. the zones were Fresnel zones. The difference $\Delta D$ between the principal powers of a lens consisting of Fresnel zones is given by $$\Delta D = \frac{2\lambda}{r_j^2 - r_{j-1}^2} \tag{11}$$

where $r_j$ is the outer bonding radius of the j-th zone, $r_{j-1}$ is the inner bonding radius of the j-th zone and $\lambda$ is the design wavelength, as can be derived from equation (1). In equation (11) the denominator $r_j^2 - r_{j-1}^2$ is identical for all annular zones.

It is not necessary, though, that all annular zones of a lens according to the present invention exhibit the same zone areas, i.e. a lens according to this invention may comprise zones of different areas as well. Then the difference $\Delta D$ is not the same for all of the lens zones, but different differences $$\Delta D_j = \frac{2\lambda}{r_j^2 - r_{j-1}^2} \quad (11')$$

are associated with different zones j.

$\Delta D_j$ is the difference between the principal powers $D_{1,j}$ and $D_{2,j}$ associated with the parameters of the j-th zone, which principal powers, for the sake of distinction, are termed "principal zone powers" $D_{1,j}$ and $D^{2,j}$. The refractive power $D_{j,G}$ of the main sub-zone of annular zone j and the refractive power $D_{j,S}$ of annular zone j can be calculated on the basis of equations (5) and (6), wherein $\Delta D$ is replaced by $\Delta D_j$, $D_m$ is replaced by $D_{mj}=(D_{1,j}+D^{2,j})/2$, and p is replaced by $p_j$. The average value $D_{m,j}$ in the equivalent of equation (5) can then be arbitrary, in principle. It should be noted that $D_{mj}$, which is the arithmetic average of the two principal zone powers, is not to be confused with the average refractive power of the annular zone.

Of particular interest are lenses according to this invention, in which either the larger principal lens power or the smaller principal lens power, respectively, is constant for all zones of the lens. By way of example, the smaller principal lens power is called $D_1$ and the larger principal lens power is called $D_2$. In other examples the smaller of the principal lens powers may be called $D_2$, and the larger principal lens power be called $D_1$.

For example, it may be advantageous to construct a lens in which the central zones are designed such that the larger power $D_2$ is identical with the larger powers associated with all of the remaining lens zones, but in which the smaller powers associated with the central lens zones are different from the smaller powers of the remaining lens zones. Then the smaller powers associated with the j-th annular zone are given by $$D_{1,j}=D_2-\Delta D_j \quad (12)$$

and the average power (i.e. the arithmetic average of the principal zone powers $D_{1,j}$ and $D_{2,j}$) associated with the j-th zone is given by $$D_{m,j} = D_2 - \frac{\Delta D_j}{2} \quad (13)$$

Lens dimensioning, and in particular the calculation of the refractive powers in the main sub-zones and phase sub-zones, respectively, are done on the basis of equations (5) through (6''') above, depending on which type of lens is chosen.

As a particular example, a lens comprising zones with a constant larger power $D_2=-2$ diopters, and variable smaller powers is presented. The average refractive powers of the annular zones should be the variable smaller powers. The key values of this lens are given in Table 1.

TABLE 1

| Zone j | outer zone radius (mm) mm | phase sub-zone fraction $p_i$ | Difference $\Delta D_j$ diopters | principal zone power $D_{1,j}$ diopters | principal zone power $D_{2,j}$ diopters | average power of zone j $D_{m,j}$ diopters | refr. power $D_{j,G}$ diopters | refr. power $D_{j,S}$ (z = 0.61) diopters |
|---|---|---|---|---|---|---|---|---|
| 1 | 0.606 | 0.200 | 3.000 | −5.000 | −2.000 | −3.500 | −3.171 | −12.315 |
| 2 | 0.925 | 0.192 | 2.247 | −4.247 | −2.000 | −3.124 | −2.877 | −10.027 |
| 3 | 1.174 | 0.186 | 2.108 | −4.108 | −2.000 | −3.054 | −2.823 | −9.737 |
| 4 | 1.383 | 0.177 | 2.059 | −4.059 | −2.000 | −3.030 | −2.804 | −9.727 |
| 5 | 1.566 | 0.174 | 2.037 | −4.037 | −2.000 | −3.019 | −2.795 | −9.789 |
| 6 | 1.731 | 0.171 | 2.024 | −4.024 | −2.000 | −3.012 | −2.790 | −9.874 |
| 7 | 1.882 | 0.169 | 2.017 | −4.017 | −2.000 | −3.009 | −2.787 | −9.966 |
| 8 | 2.022 | 0.166 | 2.012 | −4.012 | −2.000 | −3.006 | −2.786 | −10.060 |
| 9 | 2.153 | 0.164 | 2.009 | −4.009 | −2.000 | −3.005 | −2.784 | −10.153 |
| 10 | 2.277 | 0.162 | 2.007 | −4.007 | −2.000 | −3.004 | −2.783 | −10.244 |
| 11 | 2.394 | 0.160 | 2.005 | −4.005 | −2.000 | −3.003 | −2.783 | −10.334 |
| 12 | 2.506 | 0.158 | 2.003 | −4.003 | −2.000 | −3.002 | −2.782 | −10.421 |
| 13 | 2.614 | 0.156 | 2.002 | −4.002 | −2.000 | −3.001 | −2.782 | −10.506 |
| 14 | 2.717 | 0.155 | 2.001 | −4.001 | −2.000 | −3.001 | −2.781 | −10.590 |
| 15 | 2.816 | 0.153 | 2.000 | −4.000 | −2.000 | −3.000 | −2.781 | −10.671 |
| 16 | 2.912 | 0.151 | 2.000 | −4.000 | −2.000 | −3.000 | −2.781 | −10.751 |
| 17 | 3.005 | 0.150 | 2.000 | −4.000 | −2.000 | −3.000 | −2.781 | −10.930 |

It can be verified from the values given in table 1 that in this lens example—called "modified lens"—the zones do not exhibit equal areas, i.e. they are not Fresnel zone, since e.g. $r_1^2 \neq r_2^2 - r_1^2$.

Figure 14:
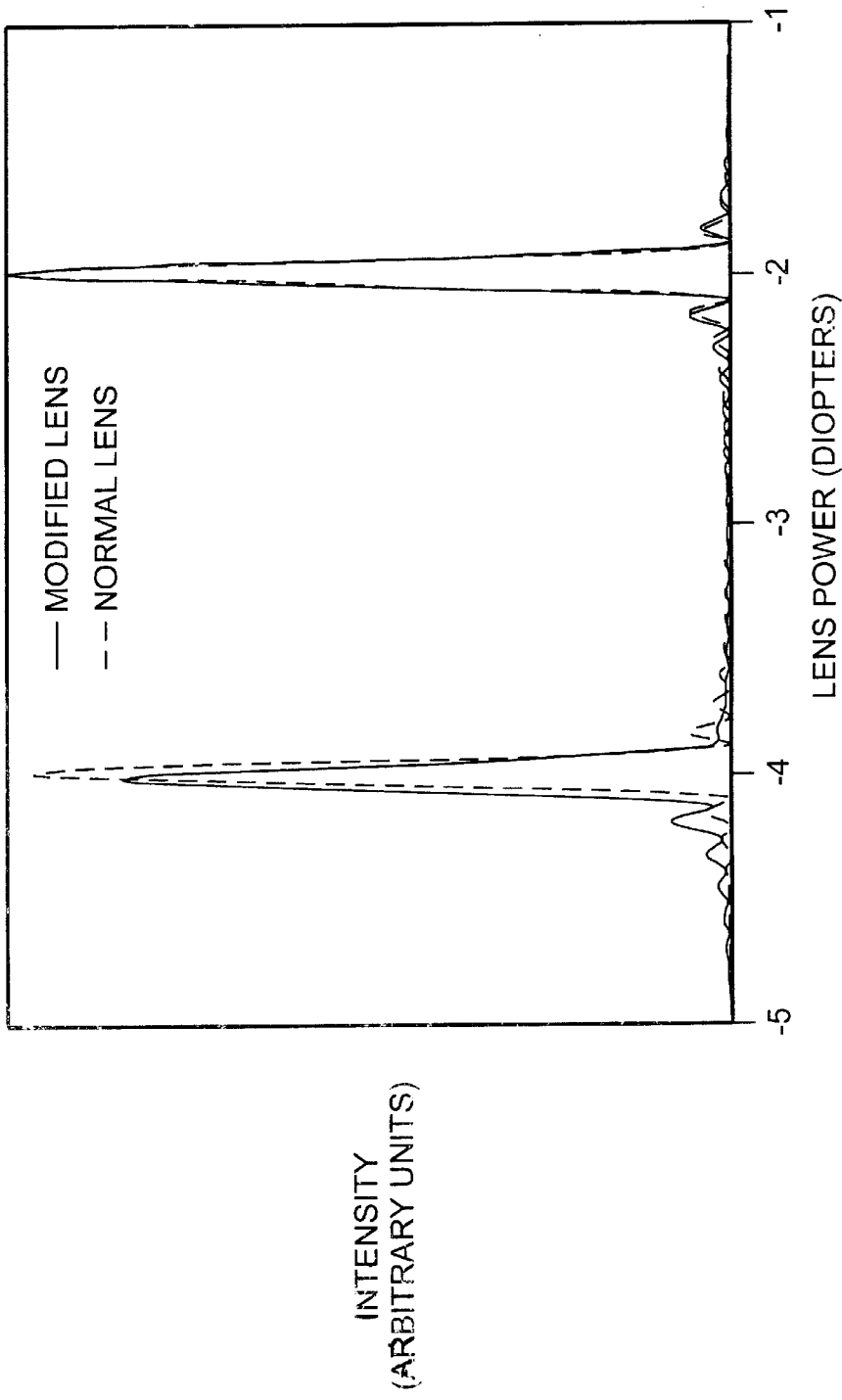
FIG. 14 shows the through focus response (TFR) for a bifocal lens for a large aperture, wherein the he annular zones of the lens do not exhibit equal areas.
Figure 15:
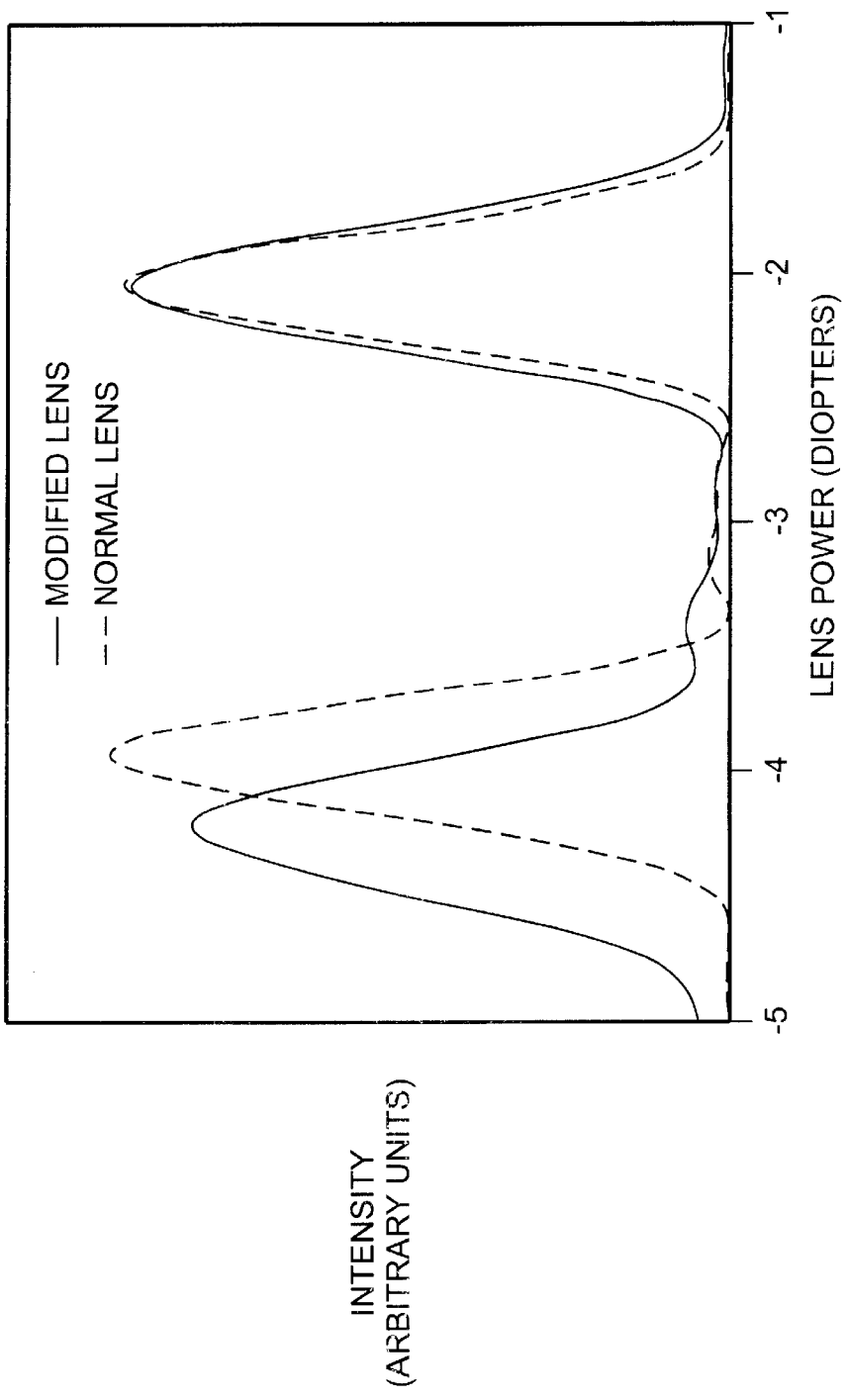
FIG. 15 shows the TFR for a bifocal lens for a small aperture, wherein the annular zones of the lens do not exhibit equal areas.

The associated through focus response (TFR) diagrams of this lens example are given in FIGS. 14 and 15 for two different lens (or pupil) diameters. For the purpose of comparison these figures also show the TFR for a lens comprising zones of equal areas, i.e. Fresnel zones, and an associated larger power of −2 diopters and an asssociated smaller power of −4 diopters; the latter lens is called "normal lens".

As can be seen from FIG. 14, the positions of the principal peaks of the "modified" and the "normal" lens, respectively are almost identical for large apertures, which in view of the choice of parameters according to table 1 is to be expected.

But within the small lens aperture of 2.5 mm (FIG. 15) a sizeable portion of zones exhibits smaller principal zone powers $D_{1,j}$ which are less than −4 diopters; consequently, the resultant intensity of the smaller aperture lens peaks at a considerably smaller lens power than the comparative "normal" lens. Such a lens design may be advantageous for certain applications, particularly in ophthalmic applications.

In other applications it may be advantageous to combine lens zones having associated smaller powers which are constant and associated larger powers which are variable. Then, the associated average powers $D_{m,j}$ (i.e. the arithmetic average of $D_{1,j}$ and $D^{2,j}$) of any of the lens zones are given by $$D_{m,j} = D_1 + \frac{\Delta D_j}{2} \tag{14}$$

and lens dimensioning is again done on the basis of equations (5) through (6'''), in which $D_m$ is replaced by $D_{m,j}$ and $\Delta D$ by $\Delta D_j$, respectively.

In general, the average power of any j-th lens zone (this average power being the arithmetic average of the two principal zone powers) of a lens according to the present invention is given by $$D_{m,j} = D_{1,j} + \frac{\Delta D_j}{2} = D_{2,j} - \frac{\Delta D_j}{2} \tag{15}$$

where $\Delta D_{1,j}$ is the smaller principal zone power associated with the j-th lens zone and $\Delta D_j$ is the difference between the larger principal zone power $D_{2,j} = D_{1,j} + \Delta D_j$ and the smaller principal zone power $D_{1,j}$ associated with the j-th lens zone. Again, lens dimensioning is done on the basis of equations (5) through (6'''), wherein $D_m$ is replaced by $D_{m,j}$ and $\Delta D$ by $\Delta D_j$, respectively.

The smaller principal power $D_1$ of the lens is then the average of the smaller principal zone powers $D_{1,j}$ and the larger principal lens power $D_2$ is the average of the larger principal zone powers $D_{2,j}$ of all lens zones.

Figure 16:
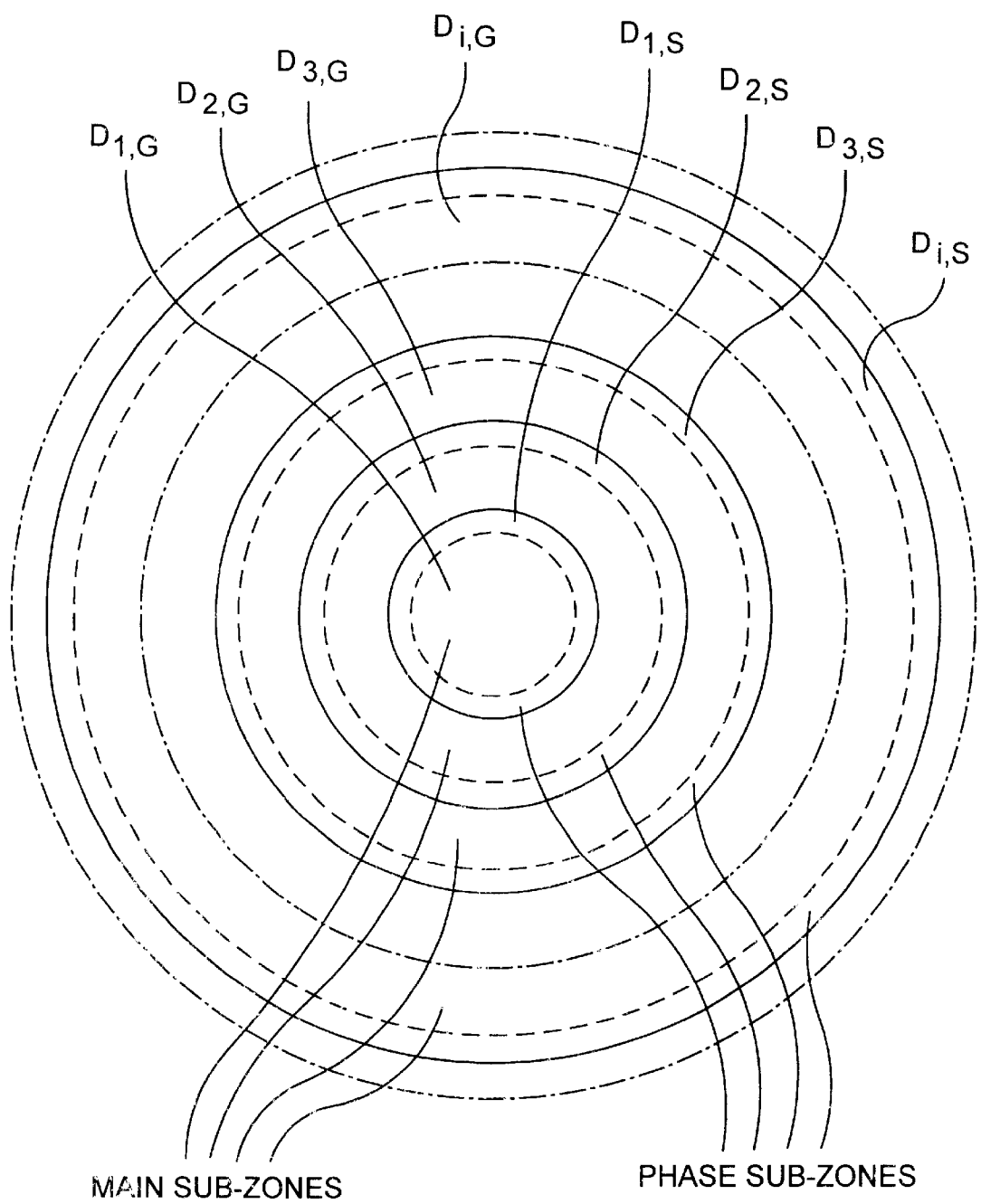
FIG. 16 is a schematic view of the annular zones of a lens subdivided into main sub-zones and phase sub-zones, wherein all sub-zones exhibit refractive powers.

FIG. 16 is a principal cross-section of a lens according to the present invention. A lens according to the present invention comprises annular zones (the innermost zone may be considered an annular zone with inner bonding radius 0) which may or may not exhibit equal areas. Every annular zone is subdivided into a main sub-zone and a phase sub-zone. The phase sub-zones cover fractions p of the annular zones, wherein these fractions p may be constant in all annular zones or be different in different annular zones. The main sub-zones of the lens are dimensioned such that they exhibit the appropriate refractive powers $D_{1,G}$, $D_{2,G}$, $D_{3,G}$, . . . , and the phase sub-zones are designed such that they exhibit the appropriate refractive powers $D_{1,S}$, $D_{2,S}$, $D_{3,S}$ . . . Both the refractive powers of the main sub-zones and of the phase sub-zones may be average refractive powers, as discussed. The set of equations provided herein allow these appropriate refractive powers to be determined. To one knowledgeable in the art, it will be understood how the various sub-zones have to be configured such that they exhibit the appropriate powers; reference is also made to the discussion in connection with FIG. 12. A lens according to the present invention is further characterized by the fact that no geometrical or optical steps are present between annular zones or sub-zones. In independence of whether the lens exhibits front surface optics or back surface optics, the lens exhibits smooth and continuous front and back surfaces, respectively, without any geometric discontinuities.

Particular mention is made that the above equations governing the design of lenses according to the present invention apply also to lenses which are immersed in some immersion medium. Particularly, the above expressions for the powers in the main and phase sub-zones may be immersed powers, like e.g. in the case of intra-ocular or intra-corneal lenses. Instead of air with a refractive index 1, an optical medium of index >1 is then located in front and behind the lens. Even the case where an optical medium of index $n_b$ is in front of the lens and another optical medium of index $n_a$ is behind the lens is characterized by the above equations. Under such circumstances, a refractive power D is expressed by $D = n_b/b + n_a/a$ where "b" is the object distance and "a" is the image distance, respectively. Immersed lenses, like, for example, intra-ocular lenses, are particularly suited for back surface optics, since no smooth enveloping surface is required in such lenses, which simplifies lens dimensioning.

Finally, it is mentioned that various possibilities exist for practical lens designing: for example, if a lens having simultaneous powers −5 and −3 diopters is desired, the above equations (5), (6), (5'), (5"), (6'), (6") can be applied by setting $D_m = -4$ diopters and $\Delta D = 2$ diopters. Lenses designed in accordance with this method will exhibit practically no spherical aberration. But this is not the only way of dimensioning a lens according to the present invention. As is known in the art, the power of two lenses in contact is, to a good approximation, the sum of the individual lens powers. On the basis of this approximation, a lens with e.g. desired powers −5 and −3 diopters can also be constructed from a bifocal lens according to this invention which exhibits the simultaneous powers 0 and 2 diopters and a conventional monofocal lens of −5 diopters. Then, in the above equations, $D_m$ would be +1 diopter and $\Delta D = 2$ diopters, as before. The appropriate monofocal lens with −5 diopters (the "shifting power") would have to be designed using standard techniques. If the lens providing the shifting power is a spherical lens, the two resulting powers of −5 and −3 diopters would also exhibit spherical aberration, which might be a desired feature. Thus, it will be apparent to those skilled in the art that the multifocal lens formed in accordance with the present invention may be combined with any other type of lens to achieve a desired result.

Lenses according to the present invention are also suitable to replace e.g. diffractive lenses, since it is much easier to produce lens surfaces which are essentially smooth than lenses with saw tooth like steps on the surface. Lenses according to the present invention can be employed in all wavelength regions in which diffractive lenses are used and are suitable for both polychromatic and monochromatic, e.g. laser light applications.

Lenses according to the present invention are suitable to replace so-called refractive multifocal lenses, since, as explained, they exhibit superior optical performance. Again, lenses according to the present invention can be employed in all wavelength regions in which refractive multifocal lenses are used.

Lenses according to the present invention open the road to novel applications since they allow the attribution of at least three independent relative intensities to three equally spaced powers (see e.g. FIG. 11).

Lenses formed in accordance with the present invention can easily be made bifocal with more than 81% of the total light intensity in the two powers and one of the two main powers can be made free of chromatic aberration. Additionally, the diffractive longitudinal chromatic aberration can be distributed over the two main powers in almost arbitrary fashion with lenses according to the present invention.

Lenses according to the present invention can successfully be employed in all areas in which either refractive or diffractive bi- or multifocal lenses are presently used. Particular fields of application are the entire spectrum of ophthalmic optics, lasers and fiber optics, as well as UV and IR optics.

Since the equations governing imaging with lenses on one hand and imaging with mirrors on the other hand are essentially isomorph (see e.g. Bergmann-Schaefer, Lehrbuch der Experimentalphysik, Band 3, Optik, Berlin New York 1993, page 88), a person knowledgeable in the art can immediately use the above considerations—which apply for lenses—for imaging systems which apply mirrors, or lenses in combination with mirrors, e.g. lenses with a semitransparent reflective coating on one of its surfaces. Since the focal length of a mirror—or its inverse value, the mirror power, which for small apertures is given by 2/R, where R is the radius of curvature of the mirror—depends on the curvature of the mirror surface, a mirror can be divided into any number of annular zones and phase sub-zones can be introduced within these annular zones in strict analogy with a lens according to this invention. The mirror surface would then compare with the lens surface which is subdivided into annular zones with appropriate refractive power profiles in its sub-zones, as discussed above.

Figure 17:
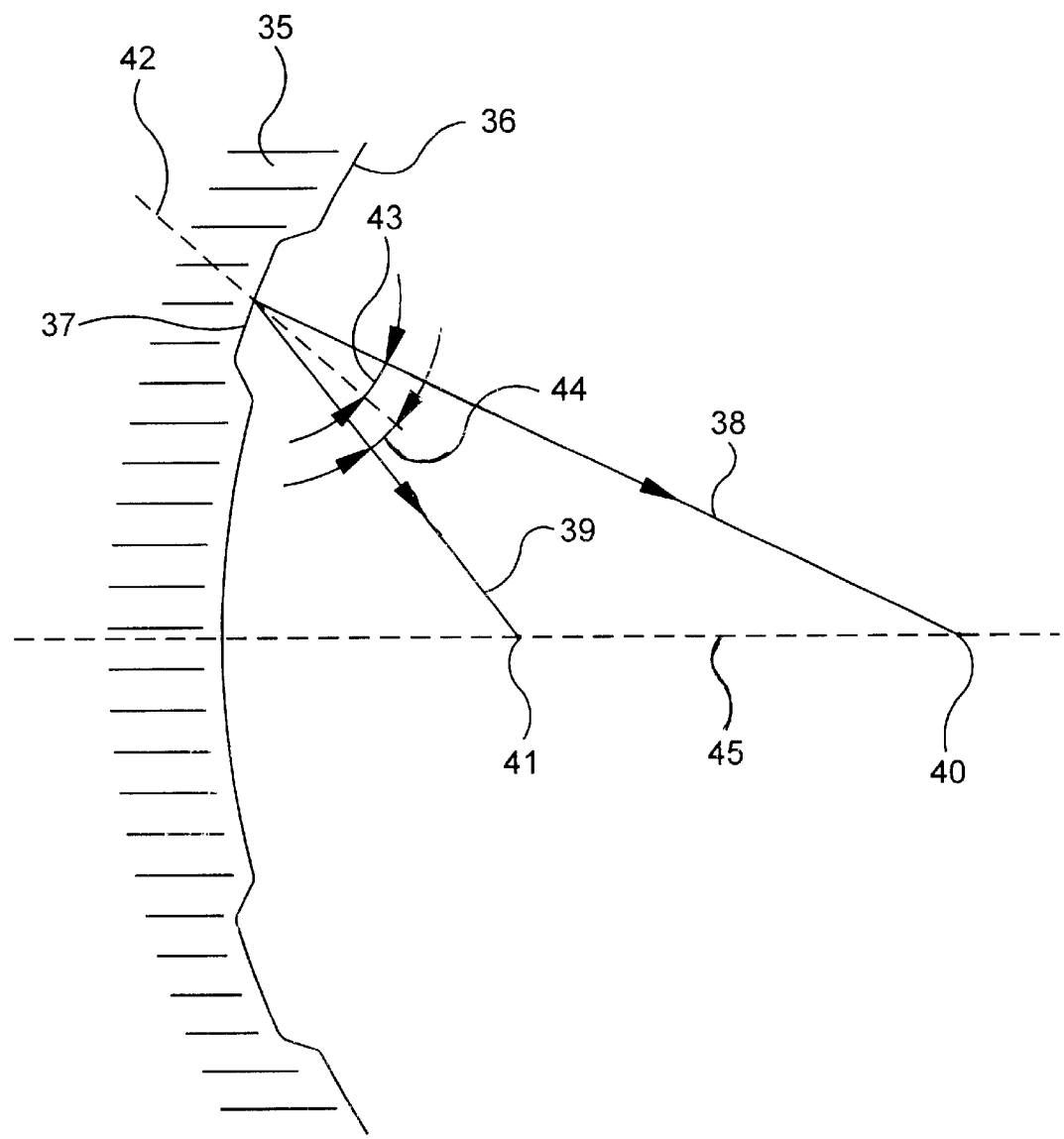
FIG. 17 is a schematic view of a detail of a mirror formed in accordance with the present invention.

Referring to FIG. 17, the general dimensioning rules for mirror sub-zones according to this invention are briefly discussed: in analogy with a lens, and as is known, a mirror power determines the position of an object point 40 and its conjugated image point 41 on the mirror axis 45. The mirror 35 has a reflecting surface 36 which is divided into zones and sub-zones. Let us assume that the surface element 37 of a sub-zone should exhibit the particular mirror power which corresponds to the positions of the object point 40 and the image point 41. Then a ray 38 originating in point 40 has to be reflected into the position of point 41. It will be appreciated that by varying the position and inclination of surface element 37 an embodiment of said mirror element will be found such that the angle 43 between the incident ray 38 and the normal 42 on the surface element 37 is equal to the angle 44 between the reflected ray 39 and the normal 42, i.e. that the reflection law is satisfied. As is apparent from this example, there exists an isomorphism between mirrors and lenses in which the reflection law of mirrors is isomorph with the refraction law of lenses, as said above.

In both FIG. 12 and FIG. 17 the situation was discussed for a lens and a mirror, respectively, in which real images are produced. It will be appreciated that the general dimensioning for the individual sub-zones will also apply for negative lenses or convex mirrors. For negative lenses the object point and the virtual image point would be located on the same side of the lens; for a negative mirror, the object point and its conjugated-virtual image point would be located on opposite sides of the reflecting mirror surface. The general dimensioning rules apply equally to these situations.

A bi- and/or multifocal mirror fabricated according to the general guidelines developed here for lenses is therefore also contemplated by the present invention. Multifocal mirrors according to the present invention can usefully be applied in many fields of optics, particularly in laser and fiber optics.

Although illustrative embodiments of the present invention have been described herein with reference to the accompanying drawings, it is to be understood that the invention is not limited to those precise embodiments, and that various other changes and modifications may be effected therein by one skilled in the art without departing from the scope of the invention.

What is claimed:

1. A multifocal lens comprising a plurality of annular zones, each of said annular zones being subdivided into at least two annular sub-zones, a main sub-zone and a phase sub-zone, said main sub-zones exhibiting refractive-powers such that the combination of said main sub-zones forms a diffractive lens with at least two principal powers and said phase sub-zones exhibit other refractive powers such that the average refractive power of each annular zone is substantially equal to at least one of the principal powers of said diffractive lens.

2. A multifocal lens as defined in claim 1, wherein the annular zones have neither geometric or optical steps therebetween.

3. A multifocal lens as defined in claim 1, wherein the annular zones comprise substantially equal area.

4. A multifocal lens as defined in claim 1, wherein the annular zones comprise different areas.

5. A multifocal lens as defined in claim 1, wherein the annular zone has no geometric steps between the main sub-zone and the phase sub-zone.

6. A multifocal lens as defined in claim 1, wherein the lens exhibits two principal powers and the main sub-zones and the phase sub-zones of the annular lens zones exhibit geometric powers such that the smaller of the principal powers is free of chromatic aberration.

7. A multifocal lens as defined in claim 1, wherein the lens exhibits two principal powers and the main sub-zones and the phase sub-zones of the annular lens zones exhibit geometric powers such that the larger of the two principal powers is free of chromatic aberration.

8. A multifocal lens as defined in claim 1, wherein the lens exhibits two principal powers and includes n annular lens zones of a lens in which the main sub-zones and the phase sub-zones of the n annular zones exhibit geometric powers such that the smaller of the principal powers is free from chromatic aberration which are combined with m lens annular zones of a lens in which the main sub-zones and the phase sub-zones of the m annular lens zones exhibit geometric powers such that the larger of the two principal powers is free from chromatic aberration, and wherein n and m are arbitrary whole numbers.

9. A multifocal lens as defined in claim 8, wherein n and m are chosen such that a fraction m/(n+m) of total longitudinal chromatic aberration of the lens is manifest in the smaller of the two principal powers and a fraction n/(n+m) of total longitudinal chromatic aberration is manifest in the larger of the two principal powers.

10. A multifocal lens as defined in claim 1, in which the main sub-zones and the phase sub-zones of odd numbered annular zones-exhibit at least two refractive powers, and in which the main sub-zones and phase sub-zones of the even numbered annular zones exhibit at least two refractive powers which are different from the two refractive powers within the odd numbered annular zones, and further wherein the average refractive power of the odd numbered annular zones are different from the average refractive power of the even numbered annular zones and one of the principal powers of the diffractive lens is substantially equal to said average refractive power of said odd numbered annular zones and the other of the principal powers of said 10 diffractive lens is substantially equal to said average refractive power of said even numbered annular zones.

11. A multifocal lens as defined in claim 10, wherein a further principal power of the diffractive lens is substantially equal to the average refractive power of all annular zones of the lens.

12. A multifocal lens as defined in claim 1, wherein at least one main sub-zone exhibits a refractive power which is identical with one of the principal powers of the lens.

13. A multifocal lens as defined in claim 1, wherein the refractive power of at least one sub-zone is an average value of a varying local, refractive power De(r) within said sub-zone, whereby r is the annular distance from the lens center within said sub-zone and $D_z(r)$ is the corresponding local refractive power.

14. A multifocal lens as defined in claim 1, wherein the lens is an ophthalmic lens.

15. A multifocal lens as defined in claim 1, wherein the lens is a contact lens.

16. A multifocal lens as defined in claim 1, wherein the lens is one of an intra-ocular lens, and an intra-corneal lens.

17. A multifocal lens as defined in claim 1, wherein the lens forms at least a portion of a spectacle lens.

18. A multifocal lens as defined in claim 1, wherein the lens is formed in combination with a conventional lens.

19. A multifocal lens exhibiting at least two principal powers $D_1$ and $D_2$ comprising a plurality of annular zones, each of said annular zones being divided into two annular sub-zones, a main sub-zone and a phase sub-zone, wherein the main sub-zone of any given annular zone exhibits a refractive power $D_G$ and the phase sub-zone of any given annular zone exhibits a refractive power $D_S$, the values for $D_G$ and $D_S$ being expressed as follows:

$$D_G = D_m \pm \Delta D \times (\tfrac{1}{2} - z)$$

and $$D_S = D_G \pm \frac{\Delta D}{p} z$$

wherein $Dm=(D_1+D_2)/2$ and $\Delta D = D_2 - D_1$, and wherein p is the fraction of the phase sub-zone of the annular zone and wherein z is an independent design parameter which determines relative intensities of $D_1$ and $D_2$.

20. A multifocal lens as defined in claim 19, wherein the annular zones have neither geometric or optical steps therebetween.

21. A multifocal lens as defined in claim 19, wherein $D_G$ of at least one main sub-zone is equal to one of $D_1$ and $D_2$.

22. A multifocal lens as defined in claim 19, wherein $D_S$ is an average power.

23. A multifocal lens as defined in claim 19, wherein $D_G$ is an average power.

24. A multifocal lens as defined in claim 19, wherein the lens is an ophthalmic lens.

25. A multifocal lens exhibiting at least two principal lens powers $D_1$ and $D_2$, the lens comprising a plurality of annular zones, each annular zone j of said annular zones being subdivided into at least two annular sub-zones, a main sub-zone and a phase sub-zone, each main sub-zone of said annular zone j exhibiting a refractive power $D_{j,G}$ and each phase sub-zone of said annular zone j exhibiting a refractive power $D_{j,S}$, and each annular zone j exhibiting an average refractive power $D_{1,j} = D_{j,G}(1-p_j) + D_{j,S} \times p_j$, wherein $p_j$ is the fraction of the phase sub-zone of the entire annular zone j, wherein the average refractive power $D_{1,j}$ comprises a first principal zone power, each annular zone j further exhibiting an inner bonding radius $r_{j-1}$ and an outer bonding radius $r_j$, said bonding radii providing a power difference $\Delta D_j = 2\pi/(r_j^2 - r_{j-1}^2)$ of said annular zone j wherein $\lambda$ is a design wavelength, and wherein a second principal zone power $D_{2,j}$ is given by $D_{2,j} = D_{1,j} \pm \Delta D_j$, such that said principal lens power $D_1$ is the average of said principal zone powers $D_{1,j}$, and said principal lens power $D_2$ is the average of said principal zone powers $D_{2,j}$.

26. A multifocal lens as defined in claim 25, wherein the annular zones have neither geometric nor optical steps therebetween.

27. A multifocal lens as defined in claim 25, wherein there are no geometric or optical steps between adjacent main sub-zones and phase sub-zones.

28. A multifocal lens as defined in claim 25, wherein all principal zone powers $D_{1,j}$ are equal to a single value D1.

29. A multifocal lens as defined in claim 25, wherein all principal zone powers $D^{2,j}$ are equal to a single value D2.

30. A multifocal lens as defined in claim 25, wherein all principal zone powers $D_{1,j}$ are equal to a single value $D_1$, and all principal zone powers $D_{2,j}$ are equal to a single value $D_2$, respectively.

31. A multifocal lens as defined in claim 25, wherein the lens is an ophthalmic lens.

32. A multifocal mirror comprising a plurality of annular zones having no geometrc steps between said annular zones, each of said annular zones being further subdivided into at least two annular sub-zones, a main sub-zone and a phase sub-zone, said main sub-zones exhibiting mirror powers such that the combination of said main sub-zones forms a diffractive mirror with at least two principal mirror powers and said phase sub-zones exhibit other mirror powers such that the average mirror powers of each annular zone is substantially equal to at least one of the principal mirror powers of said diffractive mirror.

* * * * *